United States Patent
Del Rio et al.

(10) Patent No.: US 9,931,416 B2
(45) Date of Patent: Apr. 3, 2018

(54) ANTI-CLAUDIN 1 ANTIBODIES FOR USE IN THE TREATMENT OF COLORECTAL CANCER

(71) Applicants: INSERM (Institut National de la Sante et de la Recherche Medicale), Paris (FR); Universite de Montpellier 1, Montpellier (FR); Institut Regional du Cancer de Montpellier, Montpellier (FR)

(72) Inventors: Marguerite Del Rio, Montpellier (FR); Nadia Vezzio-Vie, Montpellier (FR)

(73) Assignees: INSERM (Institut National de la Sante et de la Recherche Medicale), Paris (FR); Universite de Montpellier, Montpellier (FR); Institut Regional du Cancer de Montpellier, Montpellier (FR)

( * ) Notice: Subject to any disclaimer, the term of this patent is extended or adjusted under 35 U.S.C. 154(b) by 0 days.

(21) Appl. No.: 14/909,238

(22) PCT Filed: Jul. 22, 2014

(86) PCT No.: PCT/EP2014/065676
§ 371 (c)(1),
(2) Date: Feb. 1, 2016

(87) PCT Pub. No.: WO2015/014657
PCT Pub. Date: Feb. 5, 2015

(65) Prior Publication Data
US 2016/0158380 A1    Jun. 9, 2016

(30) Foreign Application Priority Data
Aug. 2, 2013  (EP) .................................. 13306114

(51) Int. Cl.
*A61K 39/395*   (2006.01)
*A61K 47/48*    (2006.01)
*C07K 16/28*    (2006.01)
*C07K 16/30*    (2006.01)
*C07K 16/18*    (2006.01)
*A61K 39/00*    (2006.01)

(52) U.S. Cl.
CPC .. *A61K 47/48569* (2013.01); *A61K 47/48384* (2013.01); *C07K 16/18* (2013.01); *C07K 16/28* (2013.01); *C07K 16/3046* (2013.01); *A61K 2039/505* (2013.01); *C07K 2317/24* (2013.01); *C07K 2317/31* (2013.01); *C07K 2317/33* (2013.01); *C07K 2317/565* (2013.01); *C07K 2317/569* (2013.01); *C07K 2317/732* (2013.01); *C07K 2317/734* (2013.01)

(58) Field of Classification Search
CPC ............................ C07K 16/00–16/468; A61K 39/395–39/39558; G01N 33/574–33/57496
See application file for complete search history.

(56) References Cited

U.S. PATENT DOCUMENTS

| 8,518,408 B2 * | 8/2013 | Baumert ................ C07K 16/28 424/149.1 |
| 2002/0150574 A1 | 10/2002 | Hoevel et al. |
| 2010/0028359 A1 | 2/2010 | Gu et al. |
| 2016/0185856 A1 * | 6/2016 | Del Rio ................ C07K 16/28 424/172.1 |

FOREIGN PATENT DOCUMENTS

| EP | 1 167 387 A1 | 1/2002 |
| WO | 2010/034812 A1 | 4/2010 |

OTHER PUBLICATIONS

M.J. Kwon, Int'l J. Mol. Sci. 2013; 14:18148-80.*
Ersoz et al., Pathol. Res & Practice 2011; 207:285-89.*
Nakagawa et al., Int'l J. Oncol. 2011; 39:791-96.*
Shibutani et al., Anticancer Res. 2013; 33:3301-06.*
Kinugasa et al., Anticancer Res. 2007; 27:3729-34.*
Kinugasa et al., Anticancer Res. 2010; 30:3181-86.*
Reichert & Valge-Archer, Nat. Rev. Drug Disc. 2007; 6:349-356.*
Chan and Carter, Nature Reviews Immunology, 2010; 10:301-316.*
Hoevel et al.; "Expression and targeting of the tight junction protein CLDN1 in CLDN1-negative human breast tumor cells"; Journal of Cellular Physiology, vol. 191, No. 1, 2002, pp. 60-68.

* cited by examiner

*Primary Examiner* — Jessica H Roark
(74) *Attorney, Agent, or Firm* — Whitham Curtis & Cook, PC

(57) ABSTRACT

The present invention relates to anti-claudin 1 antibodies for use in the treatment of colorectal cancer. In particular, the present invention relates to a method of treating a colorectal cancer in a subject in need thereof comprising administering the subject with a therapeutically effective amount of an anti-claudin 1 (CLDN1) antibody.

16 Claims, 16 Drawing Sheets

E

Figure 1A:
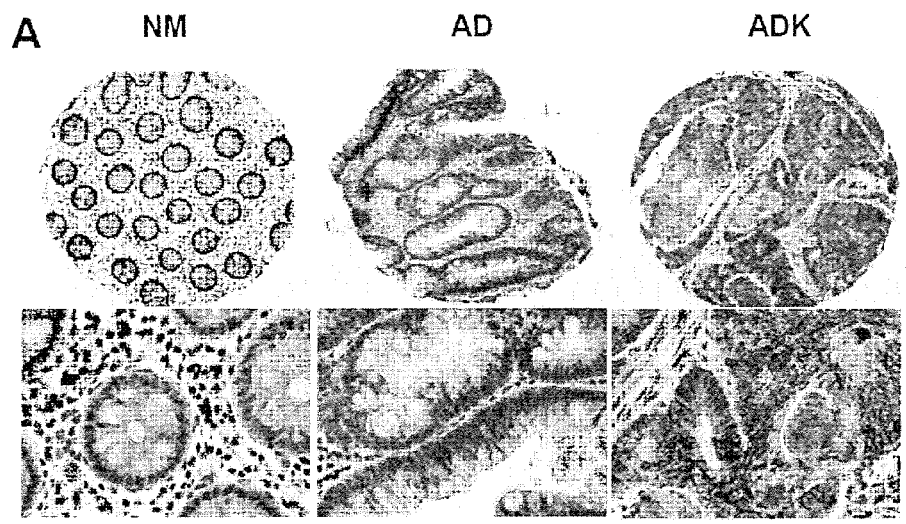

F

ANTI-CLAUDIN 1 ANTIBODIES FOR USE IN THE TREATMENT OF COLORECTAL CANCER

FIELD OF THE INVENTION

The present invention relates to anti-claudin 1 antibodies for use in the treatment of colorectal cancer.

BACKGROUND OF THE INVENTION

The CLDNs are integral membrane proteins associated with tight junctions (TJs). TJs are located at the most apical region of the lateral membrane in epithelial cell and endothelial sheets. Their two major functions are a fence function that maintains cell polarity and a paracellular barrier function that regulates the diffusion of solutes (Tsukita and Furuse, 2006). CLDNs interact in two different ways: laterally in the plane of the membrane (heteromeric interactions) or head to head binding between adjacent cells (heterotypic interactions). They can form a complex with occludin and/or JAMs. They have a short intracellular N-terminal domain, four transmembrane domains, two extracellular loops and an intracellular C-terminal domain containing a phosphorylation site and a PDZ-domain-binding motif that allows claudins to interact directly with cytoplasmic scaffold proteins, such as the TJ-associated proteins MUPP1, PATJ, ZO-1, ZO-2 and ZO-3, and MAGUKs (Lal-Nag and Morin, 2009). These proteins might function as adaptors at the cytoplasmic surface of tight-junction strands to recruit other proteins including cytoskeletal and signalling molecules (Tsukita et al., 2001). A number of other cytosolic and nuclear proteins which includes regulatory proteins Rab3b, Rab13, tumor suppressors like PTEN, transcription factors like ZONAB, and HuASH1 have also been shown to interact directly or indirectly with tight junction complex (Singh et al., 2010).

CLDN1 belongs to the claudin family of proteins which consists of 24 members of closely related transmembrane proteins. CLDN1 is an emerging therapeutic target in colorectal cancer (Kominsky, 2006). CLDN1 was found overexpressed in tumor tissue compared to normal colon mucosa in several studies (including our study) and associated with tumor progression (Miwa et al., 2001; Dhawan et al., 2005; Grone et al., 2007; Huo et al., 2009). The participation of CLDN1 to neoplasia could be explained by the alteration of TJ structure and function due to aberrant tissue expression of CLDN1 or by the involvement of CLDN1 in cell signaling pathways (Singh et al., 2010). Dhawan and collab., have reported that the increase of CLDN1 in colon tumor tissues is accompanied by a delocalisation of CLDN1 from the membrane to the cytoplasm and nucleus (Dhawan et al., 2005). It was also suggested that CLDN1 could have a dual role: cell adhesion when located in the membrane and signal transduction when they are localized in the cytoplasm or the nucleus (Singh et al., 2010). Since the prior art stipulated that CLDN1 is delocalized from the membrane during tumor progression, the one skilled in the art was not able to envisage that immunotherapy based on anti-CLDN1 antibody was credible.

SUMMARY OF THE INVENTION

The present invention relates to anti-claudin 1 antibodies for use in the treatment of colorectal cancer. In particular, the present invention is defined by the claims.

DETAILED DESCRIPTION OF THE INVENTION

The inventors have investigated by immunohistochemistry the expression of CLDN1 in tissue sections from colorectal cancers. In accordance with the literature, they have shown that CLDN1 expression increased in neoplastic tissue compared to normal colon mucosa. However contrary to the prior art the inventors demonstrated that most of the adenocarcinomas displayed a membrane staining, therefore rendered credible to use CLDN1 as a target for immunotherapy for CLDN1 positive cancers. The inventors have thus selected and characterized a monoclonal antibody (i.e. 6F6C3) and made the proof of concept that it is possible to get anti-tumoral effect with such a monoclonal antibody.

An aspect of the present invention thus relates to an anti-CLDN1 antibody for use in a method for treating a colorectal cancer in a subject in need thereof.

The term "Claudin-1" or "CLDN1" has its general meaning in the art and refers to the integral membrane protein associated with tight junction claudin-1. The CLDN1 has been first identified as a 22-kD polypeptide from isolated chicken liver junction fractions and cDNAs encoding their mouse homologues were cloned (Furuse et al., 1998). Human cDNA of CLDN1 (aliase=SEMP1) was cloned and sequenced (Swisshelm et al., 1999). It contains four exons including 636 nucleotides. The translation gives a product of 211 amino acid residues. CLDN1 has a tetraspan membrane topology with four transmembrane regions. Intracellularly, CLDN1 exhibits a 7 N-terminal amino acids, a 12 loop amino acids and a 27 C-terminal amino acids. The extracellular loop (ECL) 1 consists of 53 amino acids with two conserved cysteines. The ECL2 has 27 amino acids, The term "human Claudin-1 or human CLDN1" refers to a protein having the sequence shown in NCBI Accession Number NP_066924, or any naturally occurring variants commonly found in HCV permissive human populations. The term "extracellular domain" or "ectodomain" of Claudin-1 refers to the region of the Claudin-1 sequence that extends into the extracellular space (i.e., the space outside a cell).

In some embodiments, the anti-CLDN1 monoclonal antibody of the invention is used to provide antibody dependent cellular cytotoxicity (ADCC), complement dependent cytotoxicity (CDC), or toxicity via antibody drug conjugation (ADC). In some embodiments, the anti-CLDN1 antibody may be suitable for disturbing the expression of CLDN1 at the cell surface (e.g. by provoking internalization of CLDN1) so that survival and tumour growth of tumor cells will be limited or inhibited.

The invention embraces antibodies or fragments of anti-CLDN1 antibodies.

According to the invention, the antibodies or fragment of antibodies are directed to all or a portion of the extracellular domain of CLDN1. In some embodiments, the antibodies or fragment of antibodies are directed to an extracellular domain of CLDN1.

The term "antibody" is thus used to refer to any antibody-like molecule that has an antigen binding region, and this term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP 404, 097 and WO 93/11161; whereas linear antibodies are further described in Zapata et al. (1995). Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments.

In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with antigenic forms of CLDN1. The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes.

Briefly, the recombinant CLDN1 may be provided by expression with recombinant cell lines. CLDN1 may be provided in the form of human cells expressing CLDN1 at their surface. Recombinant forms of CLDN1 may be provided using any previously described method. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Coding, Monoclonal Antibodies: Principles and Practice: Production and Application of Monoclonal Antibodies in Cell Biology, Biochemistry and Immunology, 3rd edition, Academic Press, New York, 1996). Following culture of the hybridomas, cell supernatants are analyzed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The Fc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody.

In some embodiments, the antibody is a humanized antibody. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585,089 and 5,693,761, and WO 90/07861 also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3A of the CDRs in a three dimensional model of the antibody and is predicted to be capable of interacting with the CDRs. The above methods are merely illustrative of some of the methods that one skilled in the art could employ to make humanized antibodies. One of ordinary skill in the art will be familiar with other methods for antibody humanization.

In some embodiments, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody retains a similar antigenic specificity as the original antibody. However, using certain methods of humanization, the affinity and/or specificity of binding of the antibody may be increased using methods of "directed evolution", as described by Wu et al., /. *Mol. Biol.* 294:151, 1999, the contents of which are incorporated herein by reference.

In some embodiments, the antibody is selected among those described in WO2010034812. In particular, the antibody derives from the eight of hybridoma cell lines deposited at the DSMZ (Deutsche Sammlung von Mikro-organismen and Zellkuturen GmbH, Inhoffenstraβe 7 B, 38124 Braunschweig, Germany) on Jul. 29, 2008. They were assigned Accession Numbers DSM ACC2931, DSM ACC2932, DSM ACC2933, DSM ACC2934, DSM ACC2935, DSM ACC2936, DSM ACC2937, and DSM ACC2938. Typically, the antibody may be a humanized of the antibody obtainable from the hybridoma cell lines.

In some embodiments, the antibody is the one described in EP 1167 389 or in U.S. Pat. No. 6,627,439.

In some embodiments, the antibody comprises a heavy chain variable region comprising SEQ ID NO:2 in the H-CDR1 region, SEQ ID NO:3 in the H-CDR2 region and SEQ ID NO:4 in the H-CDR3 region; and a light chain variable region comprising SEQ ID NO:6 in the L-CDR1 region, SEQ ID NO:7 in the L-CDR2 region and SEQ ID NO:8 in the L-CDR3 region.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

Thus, as will be apparent to one of ordinary skill in the art, the present invention also provides for F(ab') 2 Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The various antibody molecules and fragments may derive from any of the commonly known immunoglobulin classes, including but not limited to IgA, secretory IgA, IgE, IgG and IgM. IgG subclasses are also well known to those in the art and include but are not limited to human IgG1, IgG2, IgG3 and IgG4.

In some embodiments, the antibody is an antibody drug-conjugate. An "anti-CLDN1 antibody-drug conjugate" as used herein refers to an anti-CLDN1 monoclonal antibody according to the invention conjugated to a therapeutic agent. Such anti-CLDN1 monoclonal antibody-drug conjugates produce clinically beneficial effects on CLDN1-expressing tumor cells when administered to a subject.

In some embodiments, an anti-CLDN1 monoclonal antibody is conjugated to a cytotoxic agent, such that the resulting antibody-drug conjugate exerts a cytotoxic or cytostatic effect on a CLDN1-expressing tumor cell when taken up or internalized by the cell. Particularly suitable moieties for conjugation to antibodies are chemotherapeutic agents, prodrug converting enzymes, radioactive isotopes or compounds, or toxins. For example, an anti-CLDN1 monoclonal antibody can be conjugated to a cytotoxic agent such as a chemotherapeutic agent or a toxin (e.g., a cytostatic or cytocidal agent such as, for example, saporin, abrin, ricin A, pseudomonas exotoxin, or diphtheria toxin).

Useful classes of cytotoxic agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and-carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

Individual cytotoxic agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065 (Li et al., Cancer Res. 42:999-1004, 1982), chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, etoposide phosphate (VP-16), 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide (VM-26), 6-thioguanine, thioTEPA, topotecan, vinblastine, vincristine, and vinorelbine.

Particularly suitable cytotoxic agents include, for example, dolastatins (e.g., auristatin E, AFP, MMAF, MMAE), DNA minor groove binders (e.g., enediynes and lexitropsins), duocarmycins, taxanes (e.g., paclitaxel and docetaxel), puromycins, vinca alkaloids, CC-1065, SN-38 (7-ethyl-10-hydroxy-camptothein), topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In some embodiments, a cytotoxic agent is a conventional chemotherapeutic such as, for example, doxorubicin, paclitaxel, melphalan, vinca alkaloids, methotrexate, mitomycin C or etoposide. In addition, potent agents such as CC-1065 analogues, calicheamicin, maytansine, analogues of dolastatin 10, rhizoxin, and palytoxin can be linked to an anti-CLDN1-expressing antibody.

In specific variations, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP (dimethylvaline-valine-dolaisoleuine-dolaproine-phenylalanine-p-phenylenediamine), MMAF (dovaline-valine-dolaisoleunine-dolaproine-phenylalanine), and MAE (monomethyl auristatin E). The synthesis and structure of auristatin E and its derivatives are described in U.S. Patent Application Publication No. 20030083263; International Patent Publication Nos. WO 2002/088172 and WO 2004/010957; and U.S. Pat. Nos. 6,884,869; 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In other variations, the cytotoxic agent is a DNA minor groove binding agent. (See, e.g., U.S. Pat. No. 6,130,237.) For example, in some embodiments, the minor groove binding agent is a CBI compound. In some embodiments, the minor groove binding agent is an enediyne (e.g., calicheamicin).

In some embodiments, an antibody-drug conjugate comprises an anti-tubulin agent. Examples of anti-tubulin agents include, for example, taxanes (e.g., Taxol® (paclitaxel), Taxotere® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin. In some embodiments, the cytotoxic agent is a maytansinoid, another group of anti-tubulin agents. For example, in specific embodiments, the maytansinoid is maytansine or DM-1 (ImmunoGen, Inc.; see also Chari et al., Cancer Res. 52:127-131, 1992).

In some embodiments, the cytotoxic agent is an antimetabolite. The antimetabolite can be, for example, a purine antagonist (e.g., azathioprine or mycophenolate mofetil), a dihydrofolate reductase inhibitor (e.g., methotrexate), acyclovir, gangcyclovir, zidovudine, vidarabine, ribavarin, azidothymidine, cytidine arabino side, amantadine, dideoxyuridine, iododeoxyuridine, poscarnet, or trifluridine.

In some embodiments, an anti-CLDN1 monoclonal antibody is conjugated to a pro-drug converting enzyme. The pro-drug converting enzyme can be recombinantly fused to the antibody or chemically conjugated thereto using known methods. Exemplary pro-drug converting enzymes are carboxypeptidase G2, beta-glucuronidase, penicillin-V-amidase, penicillin-G-amidase, beta-lactamase, beta-glucosidase, nitroreductase and carboxypeptidase A.

Techniques for conjugating molecule to antibodies, are well-known in the art (See, e.g., Amon et al., "Monoclonal Antibodies For Immunotargeting Of Drugs In Cancer Therapy," in Monoclonal Antibodies And Cancer Therapy (Reisfeld et al. eds., Alan R. Liss, Inc., 1985); Hellstrom et al., "Antibodies For Drug Delivery," in Controlled Drug Delivery (Robinson et al. eds., Marcel Deiker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radiolabeled Antibody In Cancer Therapy," in Monoclonal Antibodies For Cancer Detection And Therapy (Baldwin et al. eds., Academic Press, 1985); and Thorpe et al., 1982, Immunol. Rev. 62:119-58. See also, e.g., PCT publication WO 89/12624.) Typically, the nucleic acid molecule is covalently attached to lysines or cysteines on the antibody, through N-hydroxysuccinimide ester or maleimide functionality respectively. Methods of conjugation using engineered cysteines or incorporation of unnatural amino acids have been reported to improve the homogeneity of the conjugate (Axup, J. Y., Bajjuri, K. M., Ritland, M., Hutchins, B. M., Kim, C. H., Kazane, S. A., Halder, R., Forsyth, J. S., Santidrian, A. F., Stafin, K., et al. (2012). Synthesis of site-specific antibody-drug conjugates using unnatural amino acids. Proc. Natl. Acad. Sci. USA 109, 16101-16106; Junutula, J. R., Flagella, K. M., Graham, R. A., Parsons, K. L., Ha, E., Raab, H., Bhakta, S., Nguyen, T., Dugger, D. L., Li, G., et al. (2010). Engineered thiotrastuzumab-DM1 conjugate with an improved therapeutic index to target humanepidermal growth factor receptor 2-positive breast cancer. Clin. Cancer Res. 16, 4769-4778.). Junutula et al. (2008) developed cysteine-based site-specific conjugation called "THIOMABs" (TDCs) that are claimed to display an improved therapeutic index as compared to conventional conjugation methods. Conjugation to unnatural amino acids that have been incorporated into the antibody is also being explored for ADCs; however, the generality of this approach is yet to be established (Axup et al., 2012). In particular the one skilled in the art can also envisage Fc-containing polypeptide engineered with an acyl donor glutamine-containing tag (e.g., Gln-containing peptide tags or Q-tags) or an endogenous glutamine that are made reactive by polypeptide engineering (e.g., via amino acid deletion, insertion, substitution, or mutation on the polypeptide). Then a transglutaminase, can covalently crosslink with an amine donor agent (e.g., a small molecule comprising or attached to a reactive amine) to form a stable and homogenous population of an engineered Fc-containing polypeptide conjugate with the amine donor agent being site-specifically conjugated to the Fc-containing polypeptide through the acyl donor glutamine-containing tag or the accessible/exposed/reactive endogenous glutamine (WO 2012059882). Other methods for conjugating antibodies are also described in WO/2013/092998 and WO2013092983.

It may be also desirable to modify the antibody of the invention with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron P C. et al. 1992; and Shopes B. 1992)

In some embodiments, an anti-CLDN1 monoclonal antibody of the invention is used to induce antibody dependent cellular cytotoxicity (ADCC). In ADCC, monoclonal antibodies bind to a target cell (e.g., cancer cell) and specific effector cells expressing receptors for the monoclonal antibody (e.g., NK cells, CD8+ T cells, monocytes, granulocytes) bind the monoclonal antibody/target cell complex resulting in target cell death.

Accordingly, in some embodiments, an anti-CLDN1 monoclonal antibody comprising an Fc region with effector function is used to induce antibody dependent cellular cytotoxicity (ADCC) or complement dependent cytotoxicity (CDC) against a CLDN1-expressing cell. Methods for inducing ADCC generally include contacting the CLDN1-expressing cell with an effective amount an anti-CLDN1 monoclonal antibody comprising an Fc region having ADCC activity, wherein the contacting step is in the presence of a cytolytic immune effector cell expressing an Fc receptor having cytolytic activity. Immune effector cells expressing cytolytic Fc receptors (e.g., FcγRIIIα or CD16) include, for example, NK cells as well certain CD8+ T cells. Methods for inducing CDC generally include contacting the CLDN1-expressing cell with an effective amount an anti-CLDN1 monoclonal antibody comprising an Fc region having CDC activity, wherein the contacting step is in the presence of complement. In related embodiments, an anti-CLDN1 monoclonal antibody comprising an Fc region with effector function, as described herein, is used to treat the patient. Such methods generally include administering to a subject an effective amount of an anti-CLDN1 monoclonal antibody comprising an Fc region having ADCC activity.

In some embodiments, the antibody according to the invention is a single domain antibody. The term "single domain antibody" (sdAb) or "VHH" refers to the single heavy chain variable domain of antibodies of the type that can be found in Camelid mammals which are naturally devoid of light chains. Such VHH are also called "Nanobody®". According to the invention, sdAb can particularly be llama sdAb.

In some embodiments, the antibodies can be monospecific, bispecific, trispecific, or of greater multispecificity. Multispecific antibodies, including bispecific and trispecific antibodies, useful for practicing the methods described herein are antibodies that immunospecifically bind to both CLDN1 and a second cell surface receptor or receptor complex that mediates ADCC, phagocytosis, and/or CDC, such as CD16/FcgRIII, CD64/FcgRI, killer inhibitory or activating receptors, or the complement control protein CD59. In a typical embodiment, the binding of the portion of the multispecific antibody to the second cell surface molecule or receptor complex enhances the effector functions of the anti-CLDN1 antibody or other CLDN1 binding agent. In some embodiment, the anti-CLDN1 antibody is a bispecific antibody. The term "bispecific antibody" has its general meaning in the art and refers to any molecule consisting of one binding site for a target antigen on tumor cells and a second binding side for an activating trigger molecule on an effector cell, such as CD3 on T-cells, CD16 (FcγRlll) on natural killer (NK) cells, monocytes and macrophages, CD89 (FcαRI) and CD64 (FcγRI) on neutrophils and monocytes/macrophages, and DEC-205 on dendritic cells. According to the invention, the bispecific antibody comprises a binding site for CLDN1. Apart from the specific recruitment of the preferred effector cell population, bispecific antibodies avoid competition with endogenous immunoglobulin G (IgG) when the selected binding site for the trigger molecule on the effector cell does not overlap with Fc-binding epitopes. In addition, the use of single-chain Fv fragments instead of full-length immunoglobulin prevents the molecules from binding to Fc-receptors on non-cytotoxic cells, such as FcγRII on platelets and B-cells, to Fc-receptors that do not activate cytotoxic cells, including FcγRlllb on polymorphonuclear leukocytes (PMN), and to inhibitory Fc-receptors, such as FcγRllb on monocytes/macrophages. Methods for making bispecific antibodies are known in the art. Traditional production of full-length bispecific antibodies is based on the coexpression of two immunoglobulin heavy chain-light chain pairs, where the two chains have different specificities (see, e.g., Milstein et al., 1983, Nature 305:537-39). Because of the random assortment of immunoglobulin heavy and light chains, these hybridomas (quadromas) produce a potential mixture of 10 different antibody molecules, of which only one has the correct bispecific structure. Similar procedures are disclosed in International Publication No. WO 93/08829, and in Traunecker et al., 1991, EMBO J. 10:3655-59. Other examples of bispecific antibodies include Bi-specific T-cell engagers (BiTEs) that are a class of artificial bispecific monoclonal antibodies. BiTEs are fusion proteins consisting of two single-chain variable fragments (scFvs) of different antibodies, or amino acid sequences from four different genes, on a single peptide chain of about 55 kilodaltons. One of the scFvs binds to tumor antigen (i.e. CLDN1) and the other generally to the a n effector cell (e.g. a T cell via the CD3 receptor. Other bispecific antibodies those described in WO2006064136. In particular the bispecific antibody is a Fab format described in WO2006064136 comprising one VH or VHH specific for CLDN1 and one VH or VHH specific for an effector cell.

For administration, the antibodies are formulated as a pharmaceutical composition. A pharmaceutical composition comprising an anti-CLDN1 monoclonal antibody or antibody-drug conjugate can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See, e.g., Gennaro (ed.), Remington's Pharmaceutical Sciences (Mack Publishing Company, 19th ed. 1995)) Formulations may further include one or more excipients, preservatives, solubilizers, buffering agents, albumin to prevent protein loss on vial surfaces, etc.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In some embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

The invention will be further illustrated by the following figures and examples. However, these examples and figures should not be interpreted in any way as limiting the scope of the present invention.

FIGURES

FIG. 1 shows CLDN1 immunochemistry on colon clinical samples A) Example of CLDN1 staining in the three types of colon tissue NM=normal mucosa; AD=Adenoma; ADK=adenocarcinoma (X100) B) CLDN1 expression assessed as labeling intensity or C) as % of labeled cells. D) Localisation of the CLDN1 is indicated for each tissue of the 45 colorectal patients. E) Western blot analysis of CLDN1 expression from 13 matched tissue samples. NM=normal mucosa; PT=primary tumor. F) Subcellular fractionation of two primary tumor sample. C=cytoplasm, M=membrane, N=nucleus. β-tubulin, CD71 and Histone H3 were used as subcellular markers.

Figure 2:
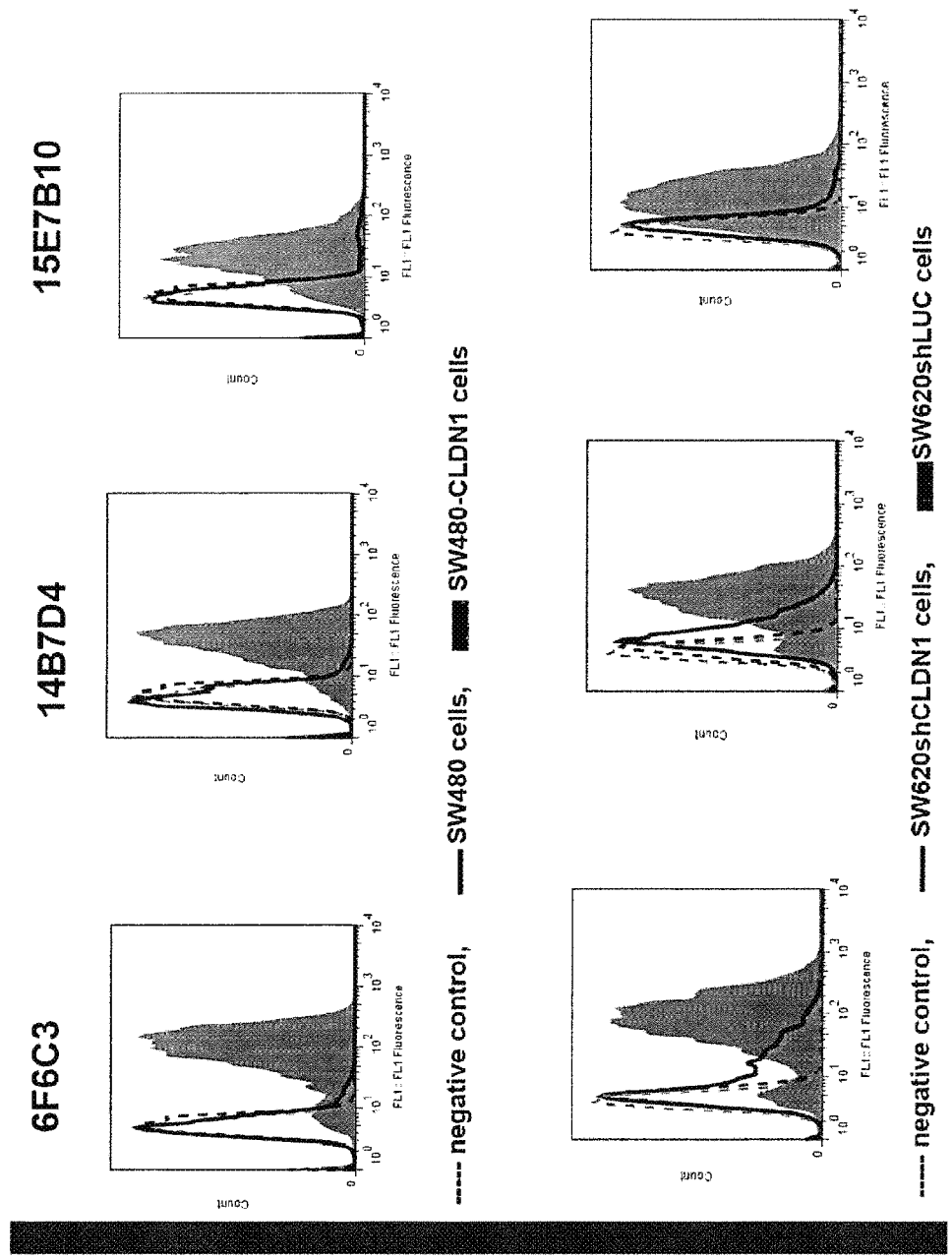

FIG. 2 shows the reactivity against CLDN1 of the three hybridomas selected. FACS histograms showing binding of selected hybridomas to CLDN1-positive cell lines (SW480-CLDN1 and SW620shLUC).

FIG. 3 shows reactivity and specificity of 6F6C3 mAb against CLDN1. A) CLDN1 expression evaluated by western blotting in different colorectal cell lines. B) GAPDH-normalized expression of CLDN1 using GeneSnap fom Syngene. C) Reactivity of purified 6F6C3 mAb (10 µg/ml) on the negative and positive-CLDN1 cell lines, determined by FACs experiments. D) The fluorescence intensities of 6F6C3 mAb binding are presented as the mean±SD of at least 3 independent experiments. E) Immunoprecipitation of CLDN1 from SW480 and SW480-CLDN1 with 6F6C3 mAb; the complexe was revealed by JAY-8 anti-CLDN1 antibody (IP=immunoprecipitation, FT=flow through). F) Immunofluorescence experiments were performed using 6F6C3 mAb as primary antibody. Images were recorded using a 63XNA objective on a Leica inverted microscope. G) Surface plasmon resonance measurements of the interaction of 6F6C3 and irrelevant antibodies on CLDN1-membrane extracts. The binding of 6F6C3 and irrelevant antibodies were performed on a Biacore 3000 instrument at 25° C. in PBS. Membrane extracts were immobilized at 2600 RU on HPA sensor chip surface according to the manufacturer's specifications. Irrelevant and 6F6C3 antibodies were injected at 660 nM over the immobilized LPS at a flow rate of 2 µL/min during 10 min followed by a 600s dissociation step with PBS running buffer.

Figure 4A:
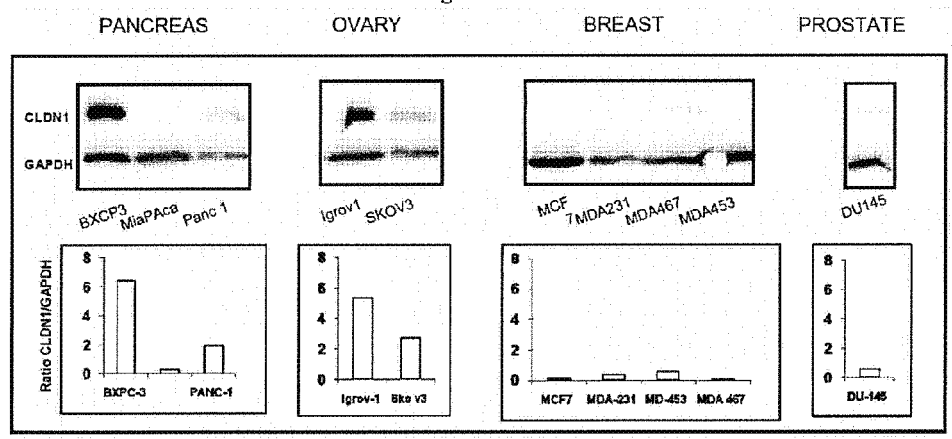
Figure 4B:
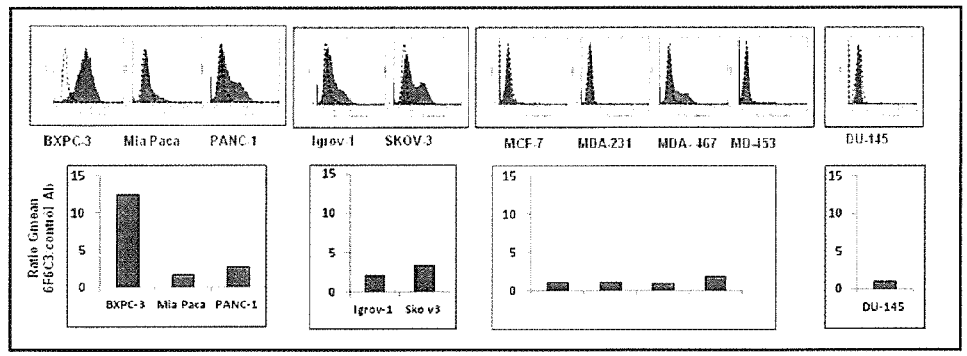

FIG. 4 shows the CLDN1 expression of several cancer cell lines and the reactivity of 6F6C3 mAb. A) Total CLDN1 expression determined by Western blot using polyclonal anti-CLDN1 antibody (JAY-8) Histograms represent the ratio CLDN1/GAPDH to normalize expression. B) Reactivity of 6F6C3 mAb (gray) or irrelevant Ab (dotted line) against cell lines. Quantification was done using Gmean ratio of 6F6C3 mAb and irrelevant antibody.

FIG. 5 shows cross-reactivity analysis of 6F6C3 mAb against other CLDNs. A). Cell lysates derived from SW480 or CLDN-transfected SW480 were tested by Western-Blotting. B) FACS histograms of the binding 6F6C3 mAb (10 µg/mL-gray histogram) or control without 6F6C3 (dashed histogram) or irrelevant antibody 35A7 (black histogram) to the different CLDNs.

FIG. 6 shows the in vitro effect of 6F6C3 mAb on cell lines survival. A) clonogenic assay on Caco-2 colorectal cell line: 250 cells are seeded on a 6-well plate and allowed to adhere overnight at 37° C. Then, one milliliter of RPMI with or without antibody (final concentration of 50 or 100 µg/ml) was added and incubated for 6 days. After 6 days more in free-medium, plates were washed; colonies were fixed (ethanol/acetic acid), stained with crystal violet (0.5% w/v) and counted using a stereomicroscope. B) Percentage of colonies of Caco2 cell line with and without treatment C) Clonogenic assay on several cell lines treated or not with 6F6C3 mAb at 100 µg/ml; histograms represent the % of inhibition (% colonies in no treated well–% colonies in treated well).

Figure 7:
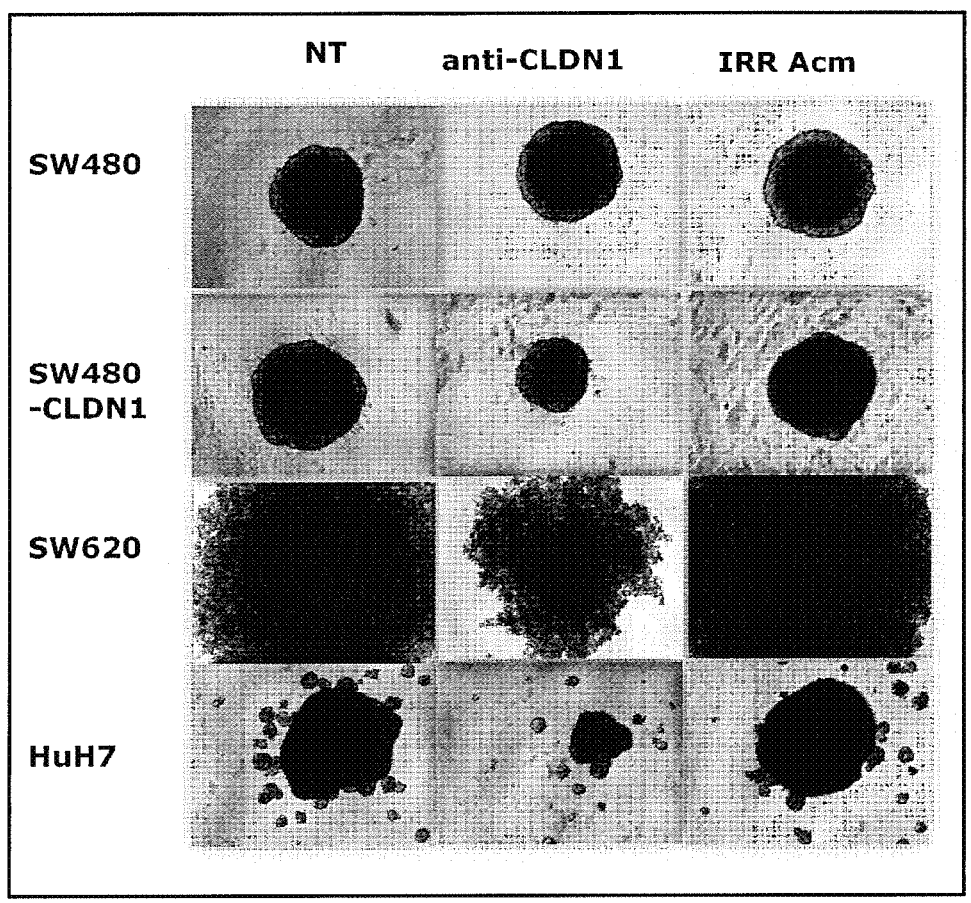

FIG. 7 shows effect of 6F6C3 mAb on 3D cell line growth. The treated cells were incubated 2 h with the mAb at 50 µg/ml (6F6C3mAb or irrelevant mAb) before seeding. Representative images of spheroids grown on Ultra low attachment plates were taken after 96 h of growth.

Figure 8A:
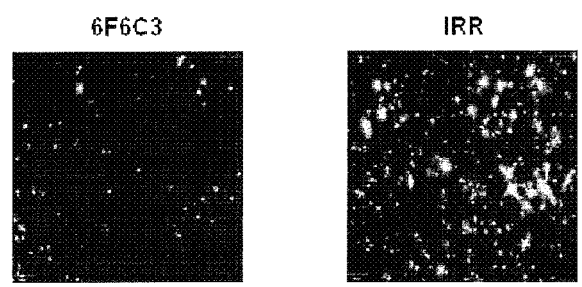
Figure 8B:
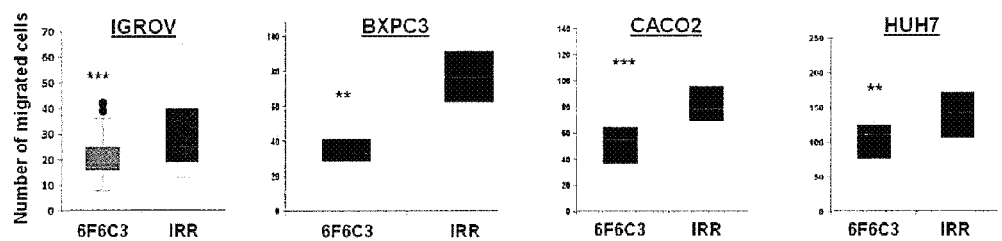

FIG. 8 shows migration assay using Boyden chambers. A) Photographs of HUH-7 cells treated or not by 6F6C3mAb at 100 µg/ml cells from the underside of Boyden chamber membrane. B) Number of migrated cells in three independent experiments for the 4 cell lines treated with 100 µg/ml of 6F6C3mAb or irrelevant mAb. Cells were preincubated with mAb 1 hour before loading.

Figure 9:
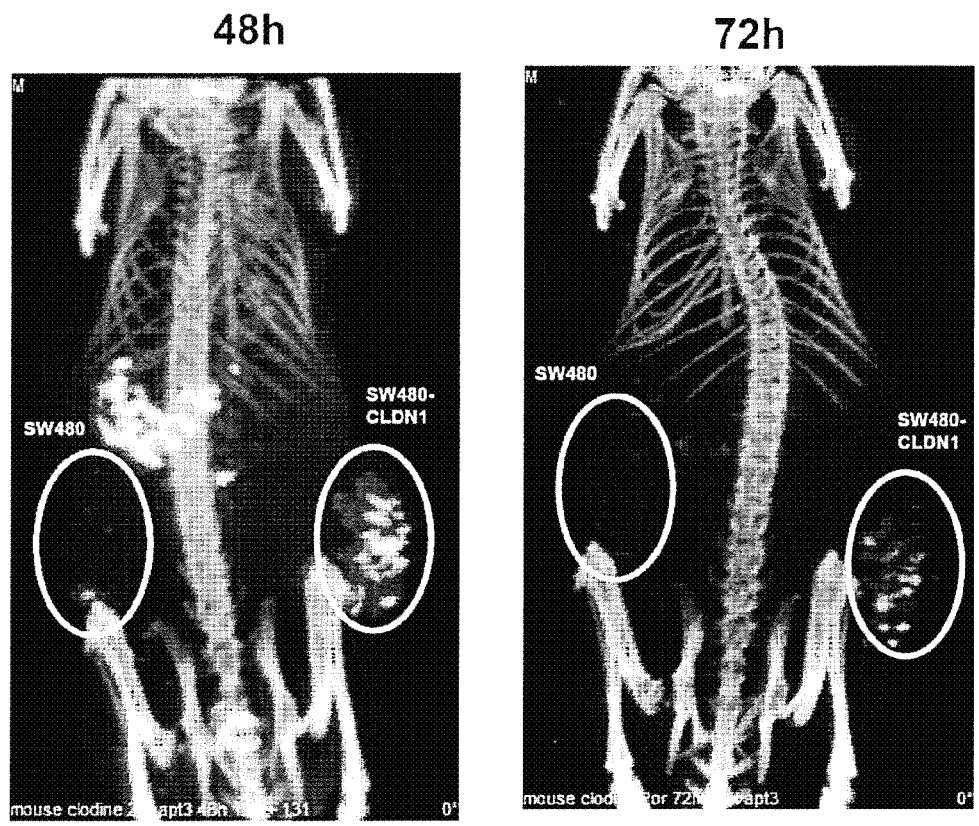

FIG. 9 shows biodistribution of $^{125}$I F6C3mAb. Grafted-mice were given intravenous injections via tail vein of 500 µCi of $^{125}$I F6C3mAb and images were acquired 2 days and 3 days after injection.

Figure 10A:
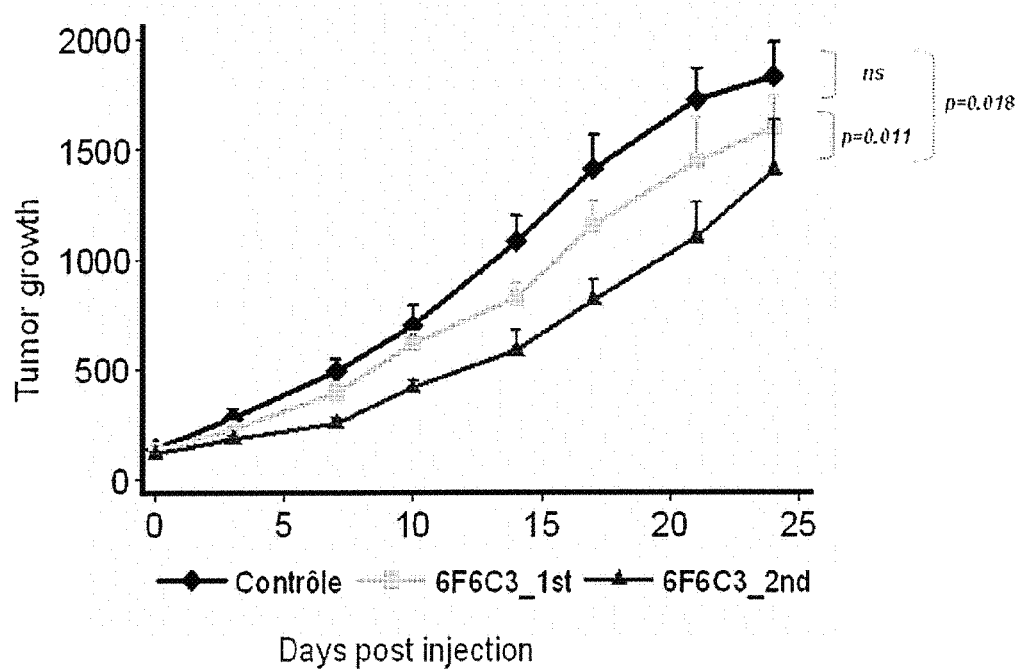
Figure 10B:
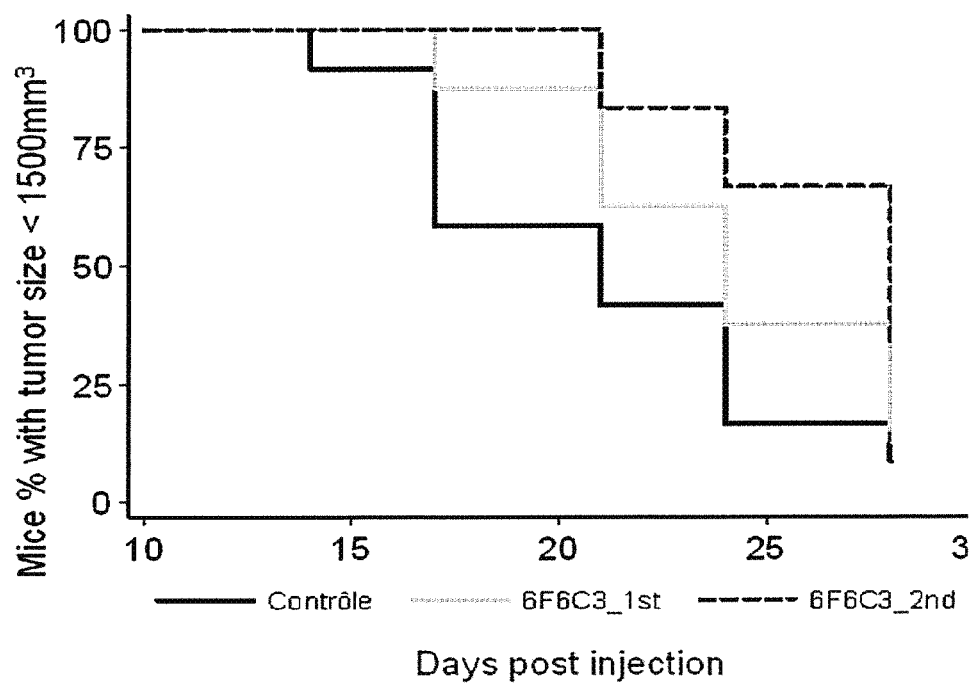

FIG. 10 shows a study of the in vivo effect of 6F6C3 mAb on the growth of SW620 xenografts in athymic nude mice. A) Tumor growth kinetics of xenografted mice with SW620 treated or not (black line) by 6F6C3 mAb at 15 mg/kg twice a week (gray line) or at 15 mg/kg three times a week (dark gray line). Treatment started when tumors reach 100 mm$^3$. B) An adapted Kaplan-Meier curves using the time taken for the tumour to reach a determined volume of 1500 mm$^3$. Black solid line corresponds to NT (non treated), gray solid line corresponds to the first experiment and gray dotted line to the second' one.

FIG. 11 shows the in vivo effect of 6F6C3 mAb on the formation of liver metastases. A) Representative SW620 metastatic tumors in liver from non-treated and 6F6C3 mAb treated mice; images were taken at the experimental endpoint (5 weeks from surgery). B) Comparison of the distribution and median of the number of metastases between both groups (p=0.08, Mann-Whitney). C) Repartition of the mice according to the number of liver metastases. <1=no metastasis or one micro metastasis; 1-10=more than 1 and less than 10 metastases; >10=more than 10 metastases.

EXAMPLE

Material & Methods

1—CLDN1 Immunochemistry on Colon Clinical Samples

Tissue micro-array (TMA) was constructed as previously described (Granci et al., 2008), using 3 tissue cores (0.6-mm diameter each) of colon cancer, of matched normal mucosa and of matched adenoma from 52 patients. Three-µm thin microns sections of the TMA were de-paraffinized and rehydrated in graded alcohols. The slides were subsequently subjected to heat-induced epitote retrieval by immersing them in a water bath with an EDTA buffer (pH 9). After neutralization of endogenous peroxidase activity, TMA sections were incubated for 60 min. with the polyclonal anti-CLDN1 antibody (JAY-8, Zymed laboratories Inc, CA, USA) or diluent only. Primary antibodies binding was visualized using the Envision® system with the Dako Autostainer® (Dako, Glostrup, Denmark). No staining was observed on the slide incubated with antibody diluent. Among the 52 cases sampled 45 samples with matched normal tissue, adenomas and tumors remains assessable after immunohistochemistry. Each spot was assigned individually for percentage of marked cells and for staining intensity (0: none; 1: faint; 2: moderate; 3 strong).

2—Cell Lines

The human colorectal cancer cell lines used were: SW480 (ATCC CCL-228), SW620 (ATCC CCL-227), Caco-2 (ATCC HTB-37), Difi ((Olive et al., 1993) a gift from Dr Montagut, HCT116 (CCL-247), LS174T (ATCC CL-188).

The other cancer cell lines used were: pancreatic cancer PANC1 (ATCC CRL1469) BXPC3 (ATCC CRL-1687), ovarian cancer SKOV-3 (ATCC HTB-77) IGROV1 (Bénard et., al 1985) and hepatocarcinoma HuH-7 (JCRB0403).

To obtain the CLDN1-positive SW480 cell line (SW480-CLDN1), we stably transfected the SW480 cell line with the human CLDN1 cDNA clone (Invitrogen MGC collection, ref 4500534, pCMV-SPORT6) using jetPRIME™ transfection reagent (Polyplus-transfection Inc., France). The stable clones were generated using geneticin as selection reagent. SW620 cell line expressing ShRNAs targeting luciferase (SW620shLUC), or CLDN1 (SW620shCLDN1) were obtained by retroviral gene transduction of the pSIREN vector. Targeting sequence are: ShLuc (from RNAi-Ready pSIREN-RetroQ vector kit, Clontech Mountain View, Calif., USA). After 24 hours from transduction, cells were selected with 1 µg/mL of puromycin and stable clones were pooled.

All the cell lines were grown in complete medium i.e., RPMI 1640 medium supplemented with 10% heat-inactivated fetal calf serum (FCS) and 2 mM L-glutamine at 37° C. under a humidified atmosphere with 5% CO2, and passaged by trypsinization using trypsin (0.5 mg/mL) EDTA (0.2 mg/mL). All culture medium supplements were purchased from Life Technologies, Inc. (Gibco BRL, Gaithersburg, Md.). For the transfected cells, geneticine (0.67%) was added in the medium.

3—Monoclonal Antibodies

Anti-CLDN1 mAbs:

Mice hybridomas were generated by immunizing BALB/c mice five times i.p. at 2-week intervals with 4 millions of murine NIH cells transiently transfected with CLDN1 referred as NIH-CLDN1 in complete Freund's adjuvant (Sigma) for the first injection, and incomplete Freund's adjuvant (Sigma) for subsequent injections. An i.v. booster injection of NIH-CLDN1 was given three months after the fifth immunization. Three days later, spleen cells from immunized mice were fused with the mouse myeloma cell line P3-X63-Ag.8.653. Supernatants from newly generated clones were screened by fluorescence-activated cell sorting (FACs) using SW480-CLDN1. The specificity for CLDN1 of supernatants was confirmed on CLDN1 positive cells as SW620 colorectal cell line.

MAbs Used as Controls:

In control experiments, anti-CEA monoclonal antibody 35A7 (specific for the CEA Gold 2 epitope, (Haskell et al., 1983; Hammarstrom et al., 1989) and an irrelevant normal mouse IgG3 (sc-3880, Santa Cruz Biotechnology)

4—Western Blot Analysis

Patients tissues samples were directly disrupted in a lysis buffer (NaCl 150 mM, 10 mM Tris, pH 7.4, 1 mM, EDTA, 1 mM EGTA, 1% SDS, 1% Triton X-100, 0.5% NP-40, 2 mM PMSF, 100 mM NaF, 10 mM sodium ortho-vanadate, one cocktail protease inhibitor tablet for 10 ml) using Mixer Mill® MM 300 (Qiagen, Valencia, Calif.). The protein concentration was determined with a Bradford assay (Pierce Coomassie Plus Protein Assay). Then, 50 µg of total protein was resolved by 12% SDS-PAGE and transferred onto nitrocellulose membranes (Whatman® Protran®, pore size 0.45 µm). The nonspecific binding sites were blocked with 5% (wt/vol) nonfat milk in PBS-T (PBS with 0.1% (vol/vol) Tween 20) for 1 hour at room temperature and then incubated overnight at 4° C. with polyclonal anti-CLDN1 antibody (JAY-8). Membranes were then washed and incubated with appropriate horeradish peroxidase-conjugated secondary antibody for 1 hr. Revelation was performed with a Chemiluminescence system (Amersham Biosciences). β-tubuline expression was used to normalisation.

5—Subcellular Protein Extraction from Tissue Samples

For each sample 20-µm thickness slides were cut with a cryotome, mixed, recovered in liquid nitrogen and gently ground with a micropestle. For subcellular protein extraction, the ProteoExtract Subcellular Proteome Extraction Kit was used according to the manufacturer's instructions (Calbiochem). 10 µg of each subcellular fraction were loaded on 12% SDS-PAGE gel. Immunoblotting was done as described above. The following primary antibodies were used: anti-CLDN1 (JAY-8), anti-CD71 (Invitrogen), anti-Histone H3 (Pierce) and anti β-tubuline (Sigma T4026)

6—Flow Cytometry Experiments

Hybridomas or mAbs binding was determined with a FACScan fluorescence-activated cell sorter (Quanta apparatus, Beckman Coulter). Cells were seeded in 25 cm$^2$ flasks ($2\times10^5$ cells/flask). After a 48-hour rest, one million cells were pelleted, Washed with PBS-1% BSA and incubated with hybridomas or mAbs, on ice for 1 h. After washing, an appropriate anti-mouse FITC conjugated monoclonal antibody ((1:60 dilution; (Invitrogen) was added (on ice for 45 mn) to detect the primary antibodies. Direct incubation of cells with the secondary antibody was used for background measurements (negative control).

7—Immunoprecipitation Studies

SW480-CLDN1 and SW480 cell culture dishes were washed with cold PBS, then adherent cells were scrapped using cold lysis buffer (25 mM Tris-HCl, 150 mM NaCl, 1 mM EDTA, 1% NP40 and one tablet of protease's inhibitors). After centrifugation, 200 µg of cell lysate was mixed with 1 ml of 6F6C3 hybridoma culture supernactant and 100 µl of G sepharose beads. The lysate beads mixture was incubated for 2 h at 4° C. under rotary agitation. The complex was eluted from beads and runned on a gel for western Blot. CLDN1 revelation was done using a commercial anti-CLDN1 antibody (JAY-8).

8—Immunofluorescence Studies

The cells were plated in culture dishes containing 12 mm glass coverslips. One day after plating, cells on the coverslip were fixed with 4% paraformaldhehyde/PBS at room temperature for 10 min and blocked with PBS containing 5% BSA at 37° C. for 30 min. The cells were incubated with 6F6C3 mAb (10 µg/ml) for 1 h. Secondary antibody was a FITC conjugated goat anti-mouse IgG (H+L) (Invitrogen). DAPI was used to stain the nucleus. Stained cells were mounted in Moviol, and images were recorded using a 63XNA objective on a Leica inverted microscope.

9—Membrane Extracts

On ice, SW480-Cldn1 cells (~$10^7$/75 cm$^2$) were washed three times with cold PBS and incubated with 1 ml of Tris 10 mM pH7.2 for 30 minutes. Then, cells were scrapped and sonicated 4 times for 5 seconds. Protein extract were centrifugated at 7000 g for 15 minutes and the supernatant was ultracentrifugated at 200 000 g during 15 minutes. The pellet was sonicated and resuspend in PBS. Protein concentration was evaluated by the BCA protein assay reagent (Pierce).

10—Establishment of Three-Dimensional Spheroid

Ultra-low attachment, 96-well round-bottomed plates (Costar) were used to form spheroids. Cells were plated at a density of $5\times10^4$ (SW480, SW480-CLDN1, SW620) or $2\times10^4$ cells/well (HuH-7). Cells aggregated and merged into three-dimensional (3D) balls with a spheroid configuration within 24 to 48 h. Images of wells were taken with a phase-contrast microscope using a 10 or 5 objective.

11—Assay for Tumor Cell Migration in Boyden Chamber

Cell migration was studied in a Boyden chamber. Briefly, cells were trypsinated, washed 3 times with serum free medium and 50 000 (IGROV, BXPC3) or 100 000 cells (Caco2, HuH-7) were added into the transwell inserts with 8 µm pore (BD Falcon® HTS Fluoroblok™ Inserts). The lower well of the chamber was filled with medium supplemented with 10% FCS. After 21 h incubation, migrated cells were stained with 4 µg/ml of calcein (Sigma-Aldrich 17783-AM) for 1 hour. The number of fluorescent migrated cells was counted in 12 different fields using ImageJ sowftware.

12—Radiolabeling and SPECT-CT Imaging $^{125}$I was obtained from Perkin Elmer, and 6F6C3 mAb was radiolabeled at the specific activity of 370 MBq/mg for SPECT imaging, using the IODO-GEN (Pierce Chemical Co.) method as previously described (Santoro et al., 2009). All animal experiments were performed in compliance with the guidelines of the French government and the standards of Institut National de la Santé et de la Recherche Médicale for experimental animal studies (agreement CEEA-LR-12052).

Nude mice, 6-8-week-old female athymic nude mice were purchased from Harlan (Gannat, France) and were acclimated for 1 wk before experimental use. They were housed at 22° C. and 55% humidity with a light-dark cycle of 12 h. Food and water were available ad libitum. The mice were force-fed with Lugol solution the day before imaging, and stable iodine was added to drinking water for the entire experimental period.

SPECT-CT imaging: Whole-body SPECT/CT images were acquired at various times (48, 72 and 96 h) after tail vein injection of 16 MBq/50 microgram radiolabeled $^{125}$I-6F6C3 mAb. Mice were anesthetized with 2% isoflurane and positioned on the bed of 4-head multiplexing multipinhole NanoSPECT camera (Bioscan Inc., Washington, USA). Energy window was centered at 28 keV with ±20% width, acquisition times were defined to obtain 30 000 counts for each projection with 24 projections. Images and maximum intensity projections (MIPs) were reconstructed using the dedicated software Invivoscope® (Bioscan, Inc., Washington, USA) and Mediso InterViewXP® (Mediso, Budapest Hungary). Concurrent microCT whole-body images were performed for anatomic coregistration with SPECT data. Reconstructed data from SPECT and CT were visualized and coregistered using Invivoscope®.

13—Intrasplenic Hepatic Colonization Model

Twenty 6-8-week-old female athymic nude mice were injected in the spleen with 2 millions of SW620-LUC cells (Luciferase-expressing SW620 cells). The spleen was removed after cell injection. On day 1, mice were randomly divided into two groups of 10 mice each. One groupe received intra-peritoneal injection of 6F6C3mAb at 15 mg/kg, the second group received only the vehicle 0.9% NaCl. Treatment with 6F6C3mAb consisted of 3 injections at 15 mg/kg per week. Once weekly, to evaluate metastatic formation and dissemination, luciferase expression was monitored by luminescence imaging after injection of luciferin. At 5 weeks from surgery, mice were sacrificed and the number and the size of metastases on the liver surface were documented.

Results:

1—CLDN1 Expression in Colon Tissues

Figure 1B:
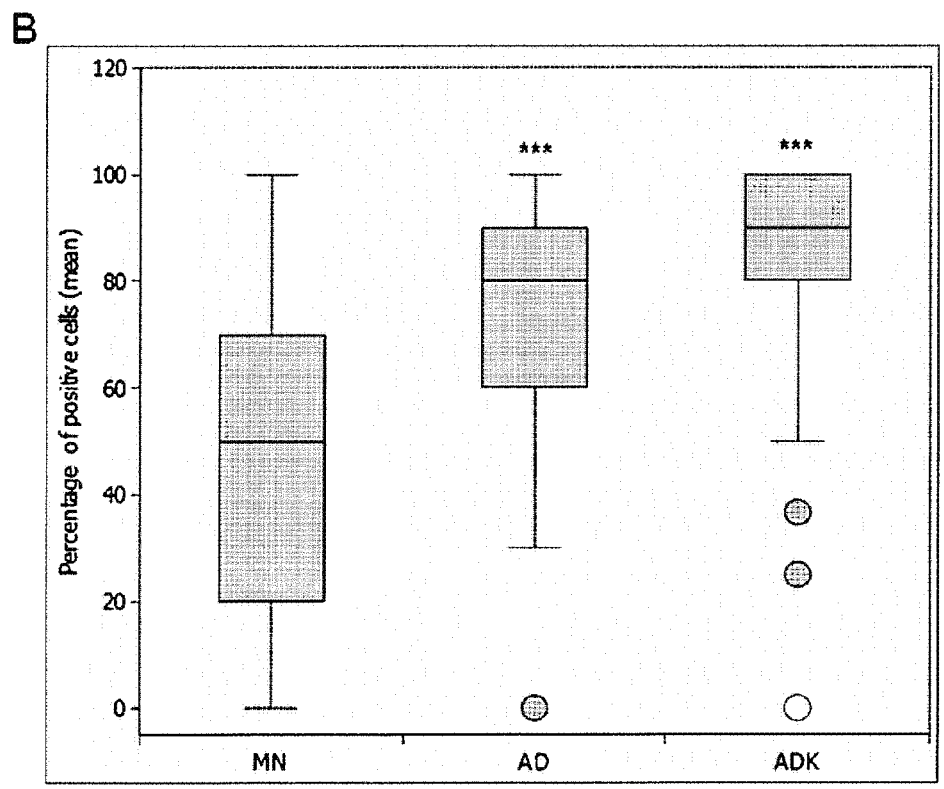
Figure 1C:
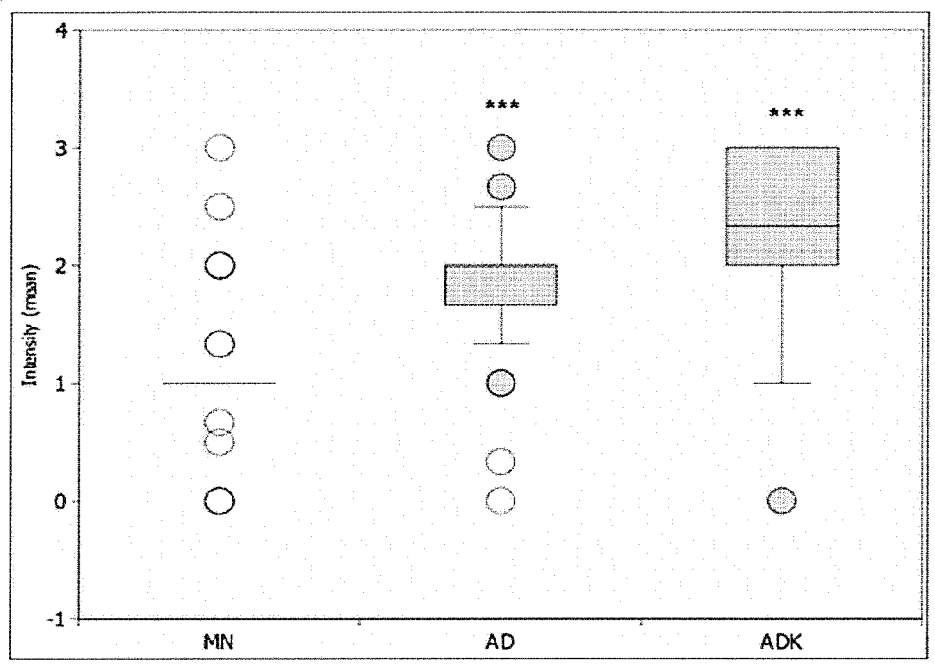
Figure 1D:
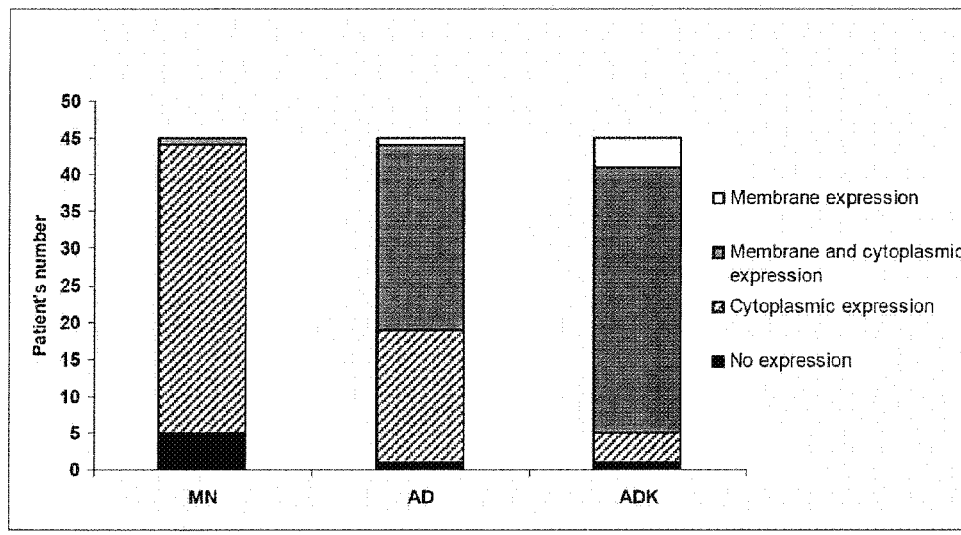
Figure 1E:
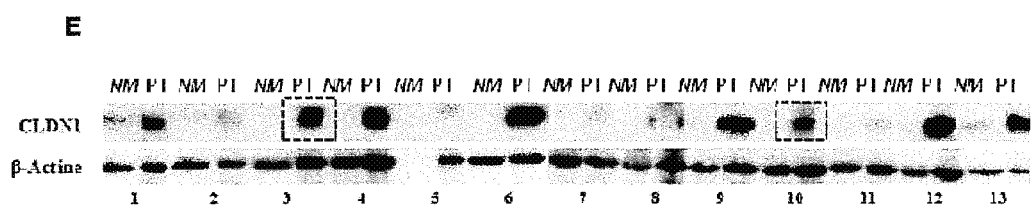
Figure 1F:
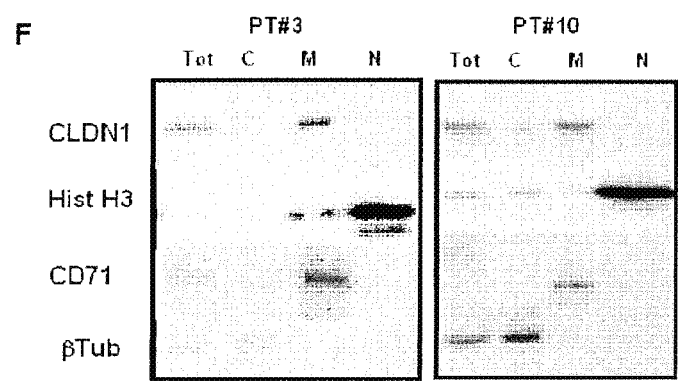

TMA from 45 colorectal cancer patients including for each patient, normal mucosa, adenoma and adenocarcinoma samples were used to determine CLDN1 expression. We showed a statistically significant increase of the CLDN1 staining from normal mucosa to adenoma (p<0.001), to adenocarcinoma (p<0.001) and from adenoma to adenocarcinoma (p=0.047 or p=0.001 for labelled cells or intensity respectively) (FIG. 1). This result was the same whatever the criterion evaluated: % of labelled cells (FIG. 1A) or mean of labelling intensity (FIG. 1B). CLDN1 immunohistochemistry signals were seen in the membrane as well as in the cytoplasm of tumors cells. The CLDN1-staining was found exclusively in the cytoplasm in normal mucosa (39/45 patients) and in half of adenomas (18/45) while in the second half of adenomas (25/45) and adenocarcinomas (36/45) we observed both membrane and cytoplasmic staining. Furthermore 9% of adenocarcinomas (4/45) displayed an exclusive membrane staining (FIG. 1C). These results show increased expression of CLDN1 in colon cancers together with a change of location.

2—Selection of mAbs Against Human CLDN1

For the selection of mAbs against CLDN1, we generated SW480-CLDN1 cells (SW480 which had acquired CLDN1 expression following stable transfection with the full-length CLDN1 cDNA) and used as a positive target. Mabs screening was performed by FACs experiments using SW480 as negative control. A confirmation screening was performed on SW620 and SW620-shCLDN1 cells. All these lines were first checked for CLDN1 expression by Western Blot. On the basis of this screening we selected three hybridomas secreting mAbs against CLDN1. After subsequent cloning by limiting dilution, we obtained three monoclonal antibodies (mAb) named 6F6C3, 14B7D4 and 15E7B10 (FIG. 2B). Antibody isotyping revealed that 6F6C3 was an IgG3k, and 14B7D4 and 15E7B10 were IgM.

3—Analysis of the Reactivity and Specificity of 6F6C3 mAb

Specificity of 6F6C3 mAb was analyzed by flow cytometry (FACS) using colorectal cell lines with differential CLDN1 expression. Western-blotting experiments were performed using total cell lysates from colorectal cancer cell lines, including SW480, SW480-CLDN1, SW620, SW620shLUC, SW620-shCLDN1, HCT116, LS174T and Caco2. Using commercial anti-CLDN1 antibody, we first evaluated the total expression of CLDN1 in the cell lines (FIG. 3A, 3B) and showed that four cell lines expressed CLDN1 (SW480-CLDN1, SW620, SW620shLUC and Caco2) while four displayed few or no CLDN1 expression (SW480, SW620-shCLDN1, LS174T HCT116). Then we tested by FACS the binding of 6F6C3 mAb on these cell lines (FIG. 3C, 3D). 6F6C3 mAb reacted only with the colon cancer cell lines expressing CLDN1. Furthermore, 6F6C3 mAb did not react with the parental SW480 cells but its reactivity was strongly increased with SW480-CLDN1. Conversely, reactivity of 6F6C3 mAb with SW620 colorectal cells was reduced by at least 85% when CLDN1 expression was knocked down by transduction with CLDN1-specific shRNA.

Figure 3A:
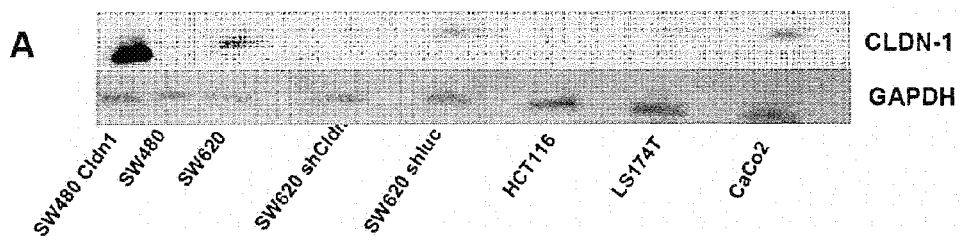
Figure 3B:
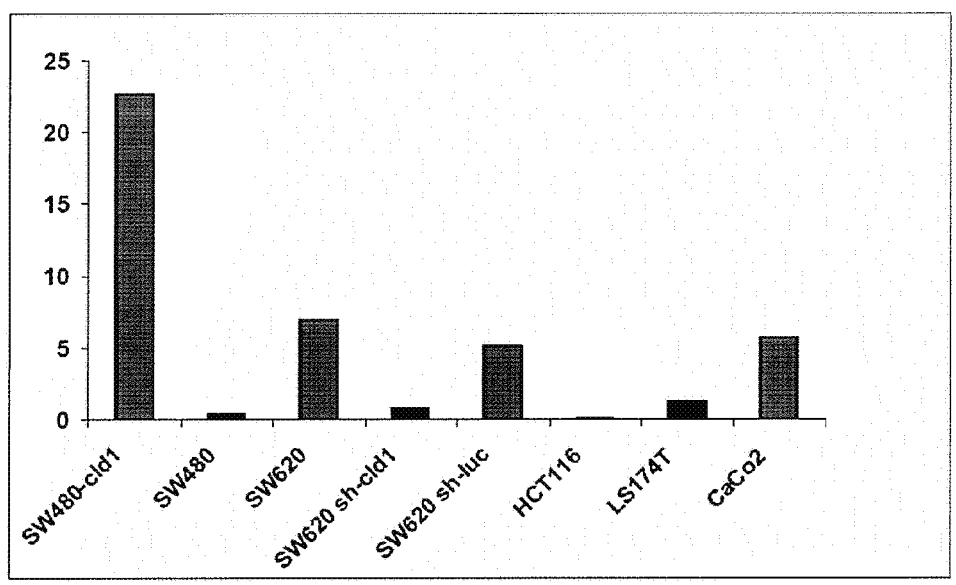
Figure 3C:
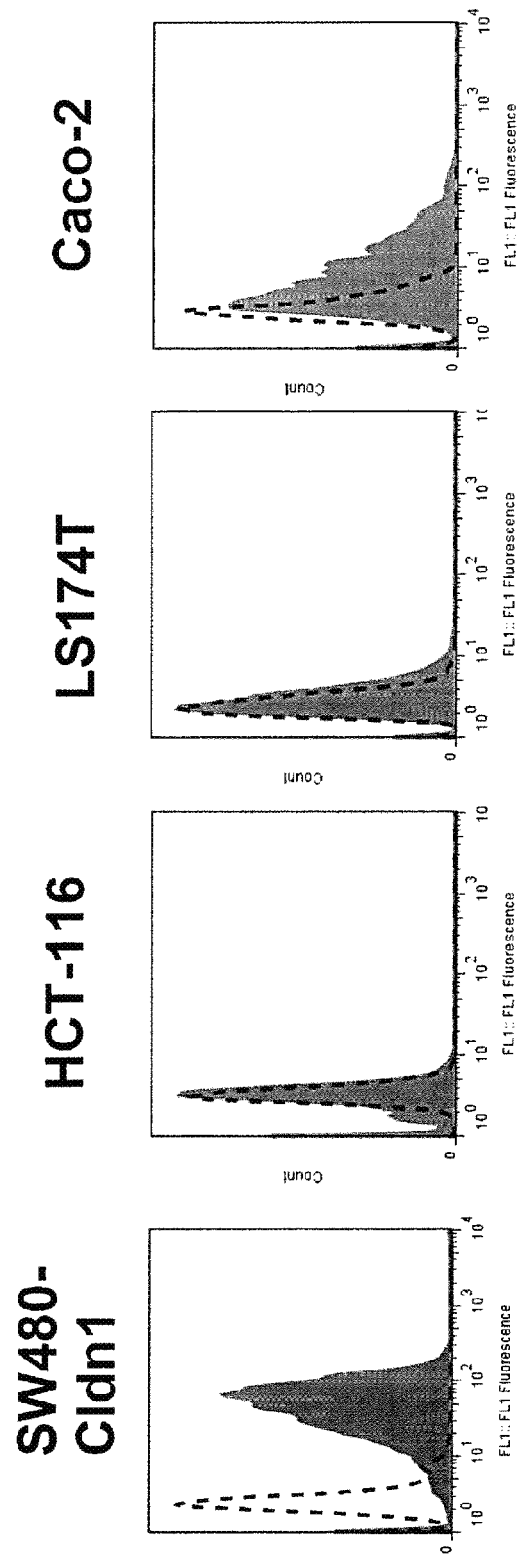
Figure 3D:
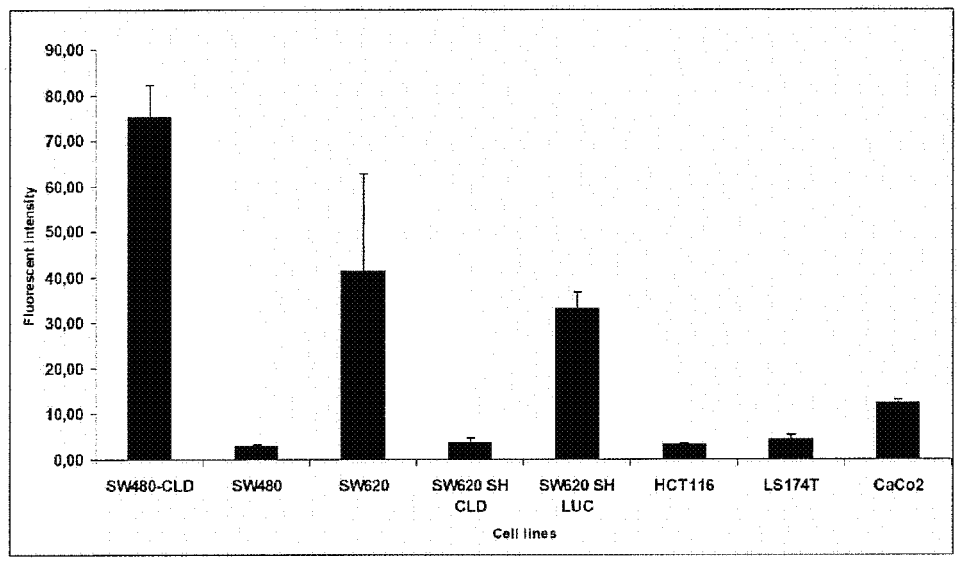
Figure 3E:
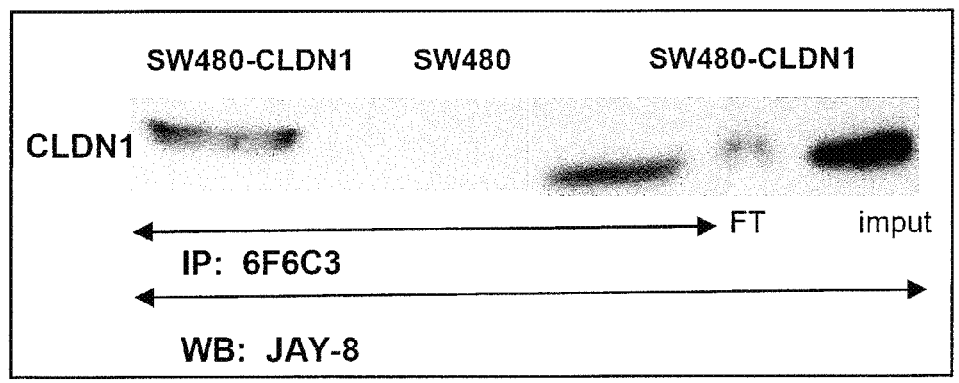

To further evaluate binding of 6F6C3 mAb to CLDN1, cell lysates were prepared from SW480-CLDN1 and SW480 and then subjected to immunoprecipitation analysis. As a result, 6F6C3 mAb specifically precipitated CLDN1 only on SW480-CLDN1 lysates (FIG. 3E).

Figure 3F:
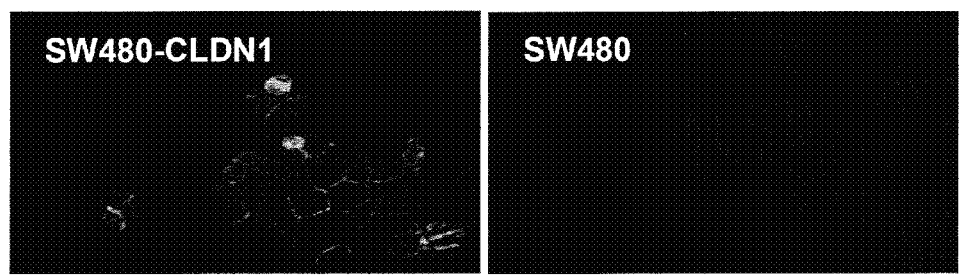

By Immunofluorescence study we showed that 6F6C3 mAb is able to bind the surface of the non-impermeabilized SW480-CLDN1 but not SW480 cells (FIG. 3F). Altogether these results suggest that 6F6C3 mAb is specific for CLDN1.

Figure 3G:
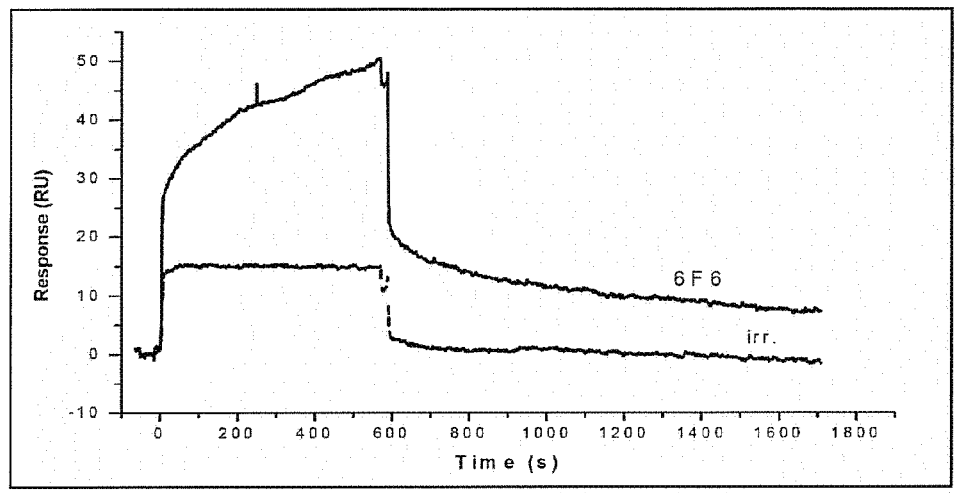

Finally, CLDN1 binding of 6F6C3 was confirmed by BIACORE analysis (FIG. 3G). BIACORE analysis has been performed using the interaction facilities located at the Cancer Research Institute Montpellier (PP2I platform, M. Pugnières). The interaction CLDN1 and 6F6C3 mAb was determined by surface plasmon resonance using BIACORE 3000 instrument (GE Healthcare, Uppsala, Sweden). CLDN1-membrane extracts were immobilised on HPA sensor chip surface. Specific interactions were seen only with 6F6C3 mAb and no with the irrelevant antibody (FIG. 3G).

We have also tested other cancer cell lines (ovarian, pancreatic, breast and prostate) for the CLDN1 expression. We first evaluated by Western blotting the total CLDN1 expression (FIG. 4A) using commercial anti-CLDN1 antibody. Thus we tested reactivity of 6F6C3 mAb by FACs. The four cell lines (BXPC3, PANC-1, SKOV-3 and IGROV-1) overexpressing CLDN1 were recognized by 6F6C3 mAb whereas any reactivity was seen with CLDN1-negative cell lines (FIG. 4B) These results confirmed the human-CLDN1 specificity of 6F6C3 mAb. In addition these cell lines can be used to test biological effect of 6F6C3 mAb on other cancer types.

4—Analysis of Cross-Reactivity with Other CLDNs

After transitory transfection on SW480 cells of human cDNA clone of CLDN8 (sc320974, Origene technologies, USA) and murine cDNA clone of CLDN1

Figure 5A:
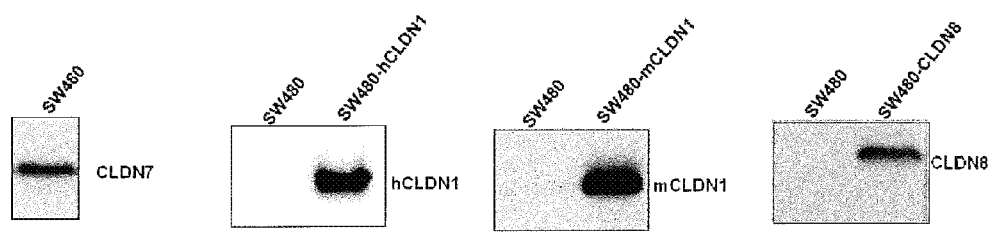
Figure 5B:
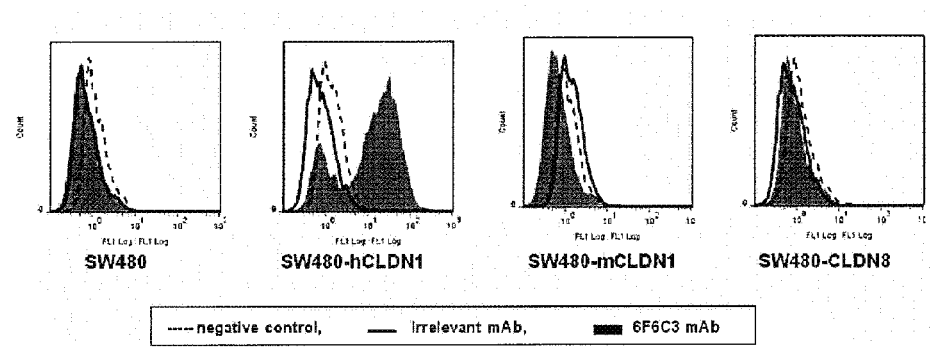

(IRAVp968A105D, LifeScience), we analysed by FACs cross-reactivity of 6F6C3 mAb. As shown in FIG. 5A, all the transfections showed an overexpression of the transfected CLDN and as already described, SW480 expressed CLDN7 as well as CLDN3 and CLDN4 (Dhawan et al., 2011). 6F6C3 mAb did not react neither with SW480-mCLDN1 nor with SW480-CLDN8 and nor with SW480 (FIG. 5B). These results indicate that 6F6C3 mAb did not recognize CLDN8, CLDN7 and probably CLDN3 and CLDN4. Furthermore 6F6C3 did not cross-react with murine CLDN1 which has 94% and 92% of identity at extracellular level with human CLDN1 (Table 1).

TABLE 1

Percentage of identity between extracellular domains of CLDNs (ClustalW2)

| CLDNs | ECL1[a] | ECL2 |
|---|---|---|
| murineCLDN1 | 94% | 92% |
| CLDN8 | 50% | 29% |
| CLDN7 | 69% | 51% |
| CLDN3 | 60% | 33% |
| CLDN4 | 62% | 29% |

[a]ECL = extracellular loop

5—In Vitro Biologic Effects of mAb6F6C3

Survival.

Figure 6A:
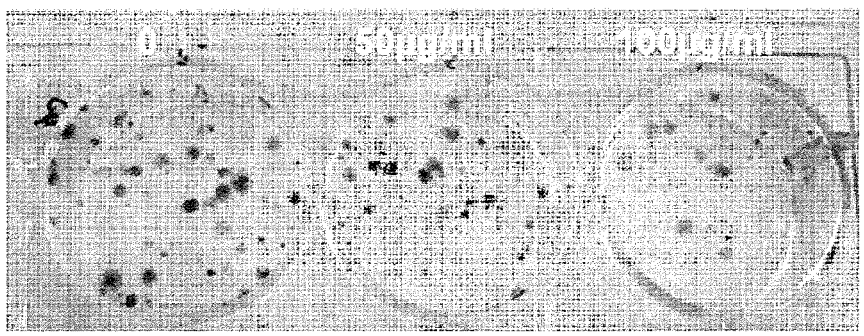
Figure 6B:
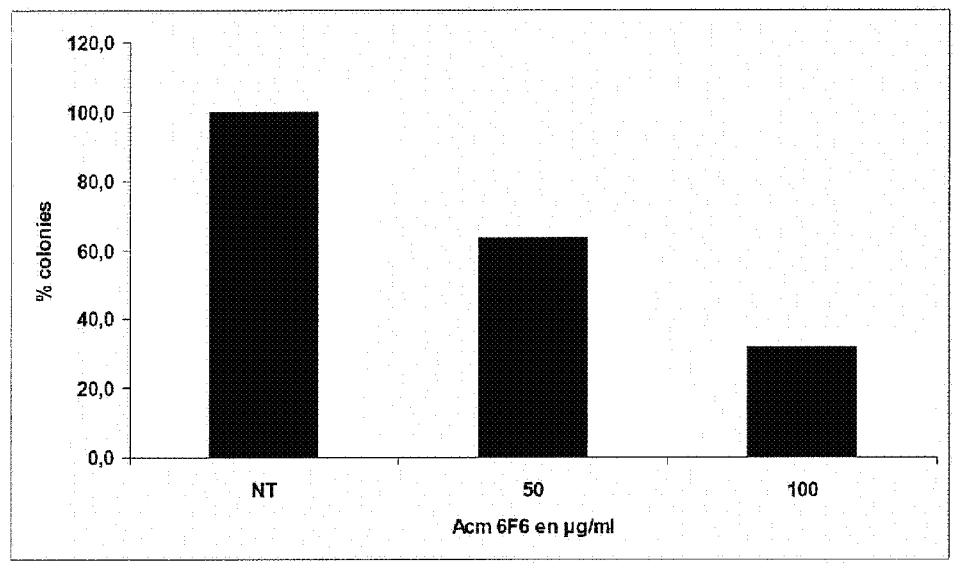
Figure 6C:
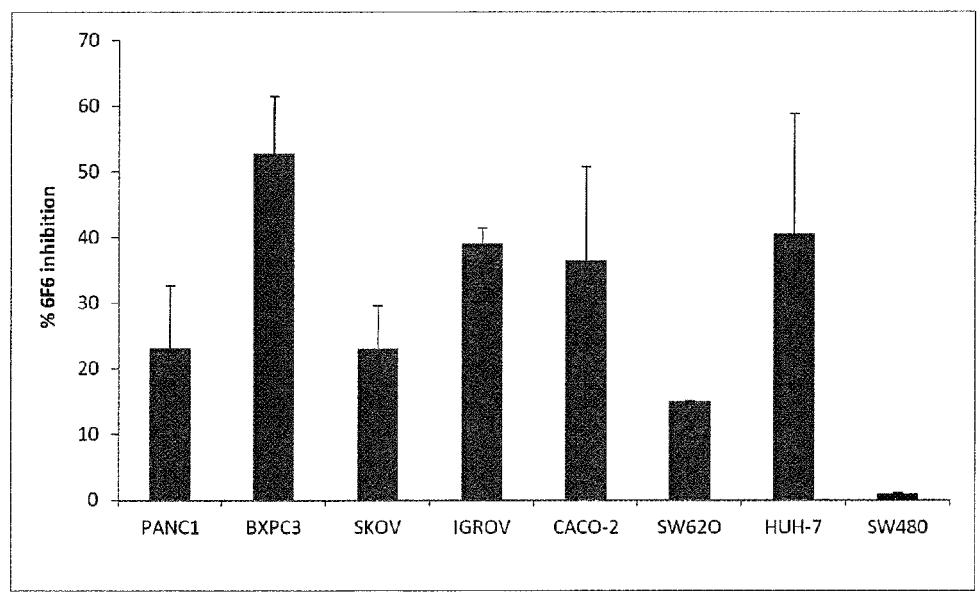

The effect of 6F6C3 mAb on survival of cells was tested by a clonogenic assay which is based on the ability of a single cell to grow into a colony (Franken et al., 2006). Treatment by 6F6C3mAb reduced the number of colony-forming cells for Caco2 colorectal cancer cells (FIG. 6A). This reduction was concentration dependent as it was of 37% for 6F6C3mAb at 50 µg/ml and of 68% for 100 µg/ml (FIG. 6B). In order to confirm that the observed effect is specific of CLD1, we performed clonogenic assay on six other cell lines overexpressing CLDN1 (BXPC3, PANC-1, SKOV-3, IGROV-1, HuH-7 and SW620) and on SW480 as negative control. As shown in FIG. 6C, 6F6C3mAb was able to inhibit the formation of colonies for all the cell lines excepted for the CLDN1-negative cell line SW480, indicating that this effect is specific of the CLDN1 binding by 6F6C3mAb.

Growth.

The effect 6F6C3 mAb on cell growth was studied on 3D culture. The shape of 3D spheres varied depending on cell line used. SW480 and SW480-CLDN1 formed single, tight, spherical and regular spheroids, HuH-7 too but less regular and accompanied by micro spheroids while SW620 formed aggregates (FIG. 7). When the cells were incubated with 6F6C3mAb, we observed a decrease of sphere size compared to the non-treated cells or cells treated with an irrelevant mAb for the three CLDN1-positive cell lines (FIG. 7). Any effect was shown on CLD1-negative cell line, SW480. These results demonstrated that 6F6C3mAb influence the cellular growth of CLDN1-positive cell lines.

Migration.

The effect 6F6C3mAb on migration was measured by a Boyden Chamber assay. Cells were treated by 6F6C3mAb or an irrelevant mAb. The results showed (FIG. 8) that 6F6C3mAb was be able to significantly affect the migration of all the CLDN1-positive cell lines tested.

Altogether, the binding of 6F6C3mAb on membrane CLDN1 affects growth and survival of CLDN1-positive cell lines as well as their migration capacity.

6—Biodistribution

To determine the tumor uptake and the ability of 6F6C3 mAb to specifically target CLDN1 in vivo we performed small-animal SPECT/CT study (single-photon emission computed tomography) (M. Busson, Plate-forme Imagerie du Petit Animal par Bioluminescence et Scintigraphie, IRCM). Two female athymic nude mice were grafted subcutaneously by injecting SW480-CLDN1 ($3 \cdot 10^6$) cells into the right flank and SW480 into the left flank. Intravenous injection of 50 µg (500 µCi) of $^{125}$I labelled-6F6C3mAb was performed once the tumor reached 100 mm³. Then CT and SPECT scans were acquired 48 h, 72 h and 96 h after injection. At 48 h, we observed a strong localisation of $^{125}$I labelled-6F6C3mAb in the SW480-CLDN1-grafted tumor and in stomach and in ladder but not in the SW480-grafted tumor. SPECT/CT imaging 72 hours after injection showed high and specific uptake of $^{125}$I labelled-6F6C3mAb only in the SW480-CLDN1-grafted tumor (FIG. 9). This result confirms in vivo the specificity of 6F6C3mAb to human CLDN1.

7—In Vivo Tumour Growth Inhibition Study:

All in vivo experiments were performed in compliance with the French guidelines for experimental animal studies (Agreement CEEA-LR-12053). Nude mice, 6-8-week-old female athymic nude mice were purchased from Harlan (Gannat, France).

SW620 ($3 \cdot 10^6$) cells were suspended in culture medium and were injected subcutaneously (s.c.) into the right flank of athymic nude mice. Tumour-bearing mice were randomized in the different groups when the tumours reached approximately the same volume (100 mm3). The mice were treated by intra-peritoneal injections (i.p.) with 0.9% NaCl or mAb6F6C3. The amounts of injected mAb were 15 mg/Kg per injection, twice a week for three weeks consecutively for the first experiment and 3 injections per week at 15 mg/Kg for the second one.

Tumour dimensions were measured bi-weekly with a caliper and the volumes calculated by the formula: D1×D2×D3/2.

The results were expressed by tumor growth kinetics of xenografted mice (FIG. 10A) and showed that mAb6F6C3 treated-groups had a significant (p=0.018) reduced growth compared to the control group. In addition this effect was dose-dependent as we observed a significant growth difference (p=0.011) between first and second experiment.

An adapted Kaplan-Meier survival curve, using the time taken for the tumour to reach a determined volume of 1500 mm³ (FIG. 10B), showed that the median delay is 7 days longer for the treated group as compared with the control NaCl group. (A median delay was defined as the time at which 50% of the mice had a tumour reaching the determined volume)

8—Intrasplenic Hepatic Colonization

Figure 11A:
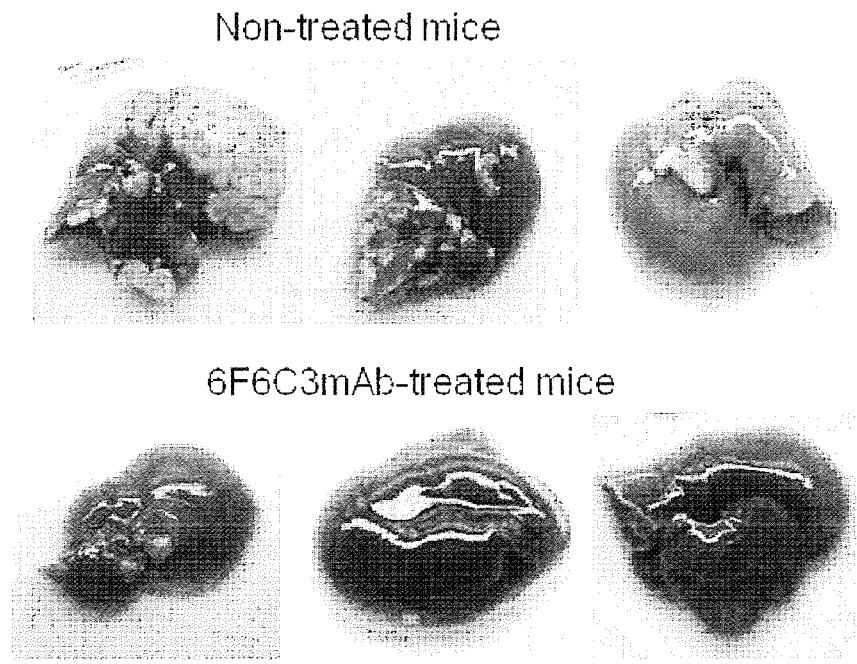
Figure 11B:
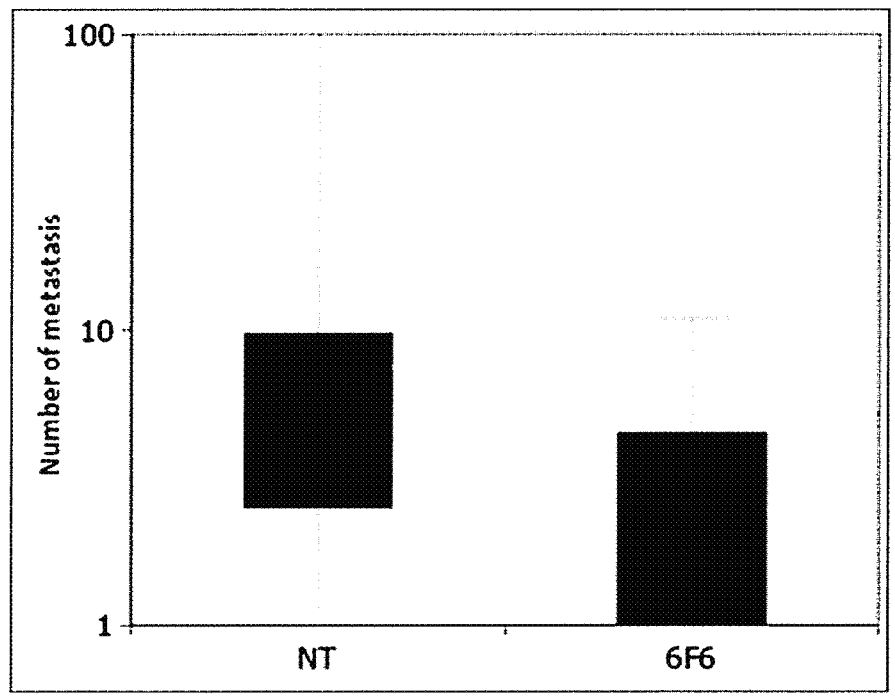
Figure 11C:
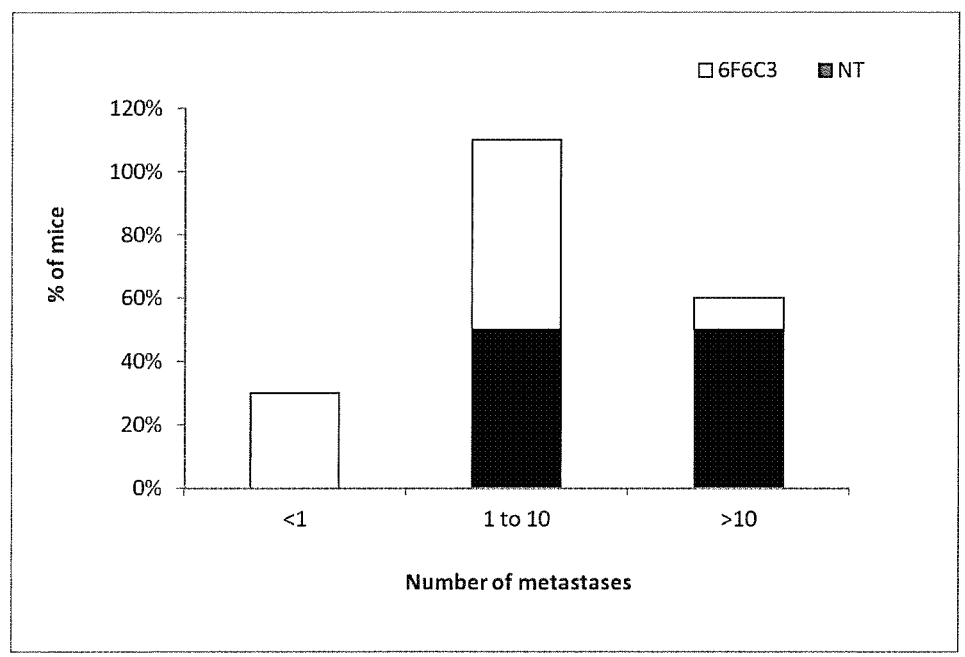

To evaluate the effects of mAb6F6C3 on the formation of metastases in liver, SW620-LUC cells were injected in mice through the intrasplenic/portal route. Mice were treated or not with 6F6C3mAb. At the experimental endpoint, livers were examined and number of metastases was determined in both groups. Consistent with previous report (Dhawan et al., 2005) SW620 metastasized to the liver. In control group, livers were shown to be invaded at higher rate compared to the treated group (FIG. 11A). Indeed, the median of number of metastases was increased in control group (FIG. 11B). Furthermore, in the control group all the mice had metastases with 50% having more than 10 liver metastases while 30% of treated group mice had no metastasis or only a micro-metastasis (FIG. 11C).

9—Sequence of mAb6F6C3:

We have cloned and characterized the variable domain of the light and heavy chains of said 6F6C3 mAb, and thus determined the complementarity determining regions (CDRs) of said antibody. The monoclonal antibody is an immunoglobulin of the IgG3 heavy chain and kappa light chain (Table 2).

TABLE 2

VH, VL and CDR domains of mAb6F6C3:

| MAb 6F6C3 domains | Sequence | SEQ ID NO |
|---|---|---|
| VH | QIQLVQSGPELKKPGETVRISCKASGYTFTTS GMQWLQKMPGKGLKWIGWINTHFGEPKYAEDF KGRFAFSLETSASTAYLQISNLKNEDTATYFC AGAGYYGSRYFDVWGAGTTVTVSS | SEQ ID NO: 1 |
| VH CDR1 | GYTFTTSG | SEQ ID NO: 2 |
| VH CDR2 | INTHFGEP | SEQ ID NO: 3 |
| VH CDR3 | AGAGYYGSRYFDV | SEQ ID NO: 4 |
| VL | DIVMTQSQKFMSTSVGDRVSITCKASQNVGTA VAWYQQKPGQSPKLLIYSASNRYTGVPDRFTG SGSGTDFTLTISNMQSEDLADYFCQQYSSYPL TFGGGTKLEIK | SEQ ID NO: 5 |
| VL CDR1 | QNVGTA | SEQ ID NO: 6 |
| VL CDR2 | SAS | SEQ ID NO: 7 |
| VL CDR3 | QQYSSYPLT | SEQ ID NO: 8 |

REFERENCES

Throughout this application, various references describe the state of the art to which this invention pertains. The disclosures of these references are hereby incorporated by reference into the present disclosure.

Aro K, Rosa L E, Bello I O, Soini Y, Mâkitie A A, Salo T, Leivo I. (2011) Expression pattern of claudins 1 and 3—an auxiliary tool in predicting behavior of mucoepidermoid carcinoma of salivary gland origin. Virchows Arch. 458:341-8.

Bénard J, Da Silva J, De Blois M C, Boyer P, Duvillard P, Chiric E, Riou G. (1985) Characterization of a human ovarian adenocarcinoma line, IGROV1, in tissue culture and in nude mice. Cancer Res. 45:4970-9.

Chao, Y.-C., Pan, S.-H., Yang, S.-C., Yu, S.-L., Che, T.-F., Lin, C.-W., Tsai, M.-S., Chang, G.-C., Wu, C.-H., Wu, Y.-Y., et al. (2009). Claudin-1 Is a Metastasis Suppressor and Correlates with Clinical Outcome in Lung Adenocarcinoma. Am. J. Respir. Crit. Care Med. 179, 123-133.

de Aquino A R, de Carvalho C H, Nonaka C F, Freitas Rde A, de Souza L B, Pinto L P. (2012) Immunoexpression of claudin-1 and Nm23-H1 in metastatic and nonmetastatic lower lip squamous-cell carcinoma. Appl Immunohistochem Mol Morphol. 20:595-601.

De Oliveira, S. S., De Oliveira, I. M., De Souza, W., and Morgado-Diaz, J. A. (2005). Claudins upregulation in human colorectal cancer. FEBS Lett 579, 6179-6185.

Dhawan, P., Ahmad, R., Chaturvedi, R., Smith, J. J., Midha, R., Mittal, M. K., Krishnan, M., Chen, X., Eschrich, S., Yeatman, T. J., et al. (2011). Claudin-2 expression increases tumorigenicity of colon cancer cells: role of epidermal growth factor receptor activation. Oncogene 30, 3234-3247.

Dhawan, P., Singh, A. B., Deane, N. G., No, Y., Shiou, S.-R., Schmidt, C., Neff, J., Washington, M. K., and Beauchamp, R. D. (2005). Claudin-1 regulates cellular transformation and metastatic behavior in colon cancer. J Clin Invest 115, 1765-1776.

Dos Reis, P. P., Bharadwaj, R. R., Machado, J., Macmillan, C., Pintilie, M., Sukhai, M. A., Perez-Ordonez, B., Gullane, P., Irish, J., and Kamel-Reid, S. (2008). Claudin 1 overexpression increases invasion and is associated with aggressive histological features in oral squamous cell carcinoma. Cancer 113, 3169-3180.

English D P, Santin A D. Claudins Overexpression in Ovarian Cancer: Potential Targets for Clostridium Perfringens Enterotoxin (CPE) Based Diagnosis and Therapy. (2013) Int J Mol Sci. 17:10412-37.

Fèvre Montange M, Vasiljevic A, Bergemer Fouquet A M, Bernier M, Champier J, Chrétien F, Figarella-Branger D, Kemeny J L, Lechapt-Zalcman E, Michalak S, Miguel C, Mokthari K, Pommepuy I, Quintin Roué I, Rousseau A, Saint-Pierre G, Salon C, Uro-Coste E, Varlet P, Kratzer I, Ghersi-Egea J F, Jouvet A. (2012) Histopathologic and ultrastructural features and claudin expression in papillary tumors of the pineal region: a multicenter analysis. Am J Surg Pathol. 36:916-28.

Franken, N. A. P., Rodermond, H. M., Stap, J., Haveman, J., and Van Bree, C. (2006). Clonogenic assay of cells in vitro. Nat Protoc 1, 2315-2319.

Furuse, M., Fujita, K., Hiiragi, T., Fujimoto, K., and Tsukita, S. (1998). Claudin-1 and -2: novel integral membrane proteins localizing at tight junctions with no sequence similarity to occludin. J. Cell Biol. 141, 1539-1550.

Granci, V., Bibeau, F., Kramar, A., Boissière-Michot, F., Thézénas, S., Thirion, A., Gongora, C., Martineau, P., Del Rio, M., and Ychou, M. (2008). Prognostic significance of TRAIL-R1 and TRAIL-R3 expression in metastatic colorectal carcinomas. Eur. J. Cancer 44, 2312-2318.

Gröne, J., Weber, B., Staub, E., Heinze, M., Klaman, I., Pilarsky, C., Hermann, K., Castanos-Velez, E., Röpcke, S., Mann, B., et al. (2007). Differential expression of genes encoding tight junction proteins in colorectal cancer: frequent dysregulation of claudin-1, -8 and -12. Int J Colorectal Dis 22, 651-659.

Hammarstrom, S., Shively, J. E., Paxton, R. J., Beatty, B. G., Larsson, A., Ghosh, R., Bormer, O., Buchegger, F., Mach, J. P., and Burtin, P. (1989). Antigenic sites in carcinoembryonic antigen. Cancer Res. 49, 4852-4858.

Haskell, C. M., Buchegger, F., Schreyer, M., Carrel, S., and Mach, J. P. (1983). Monoclonal antibodies to carcinoembryonic antigen: ionic strength as a factor in the selection of antibodies for immuno scintigraphy. Cancer Res. 43, 3857-3864.

Huo, Q., Kinugasa, T., Wang, L., Huang, J., Zhao, J., Shibaguchi, H., Kuroki, M., Tanaka, T., Yamashita, Y., Nabeshima, K., et al. (2009). Claudin-1 protein is a major factor involved in the tumorigenesis of colorectal cancer. Anticancer Res 29, 851-857.

Hsueh C, Chang Y S, Tseng N M, Liao C T, Hsueh S, Chang J H, Wu I C, Chang K P. (2010) Expression pattern and prognostic significance of claudins 1, 4, and 7 in nasopharyngeal carcinoma. Hum Pathol. 41:944-50.

Kinugasa, T., Akagi, Y., Yoshida, T., Ryu, Y., Shiratuchi, I., Ishibashi, N., and Shirouzu, K. (2010). Increased claudin-1 protein expression contributes to tumorigenesis in ulcerative colitis-associated colorectal cancer. Anticancer Res. 30, 3181-3186.

Kinugasa, T., Huo, Q., Higashi, D., Shibaguchi, H., Kuroki, M., Tanaka, T., Futami, K., Yamashita, Y., Hachimine, K., Maekawa, S., et al. (2007). Selective up-regulation of claudin-1 and claudin-2 in colorectal cancer. Anticancer Res 27, 3729-3734.

Kominsky, S. L. (2006). Claudins: emerging targets for cancer therapy. Expert Rev Mol Med 8, 1-11.

Kondoh A, Takano K, Kojima T, Ohkuni T, Kamekura R, Ogasawara N, Go M, Sawada N, Himi T. (2011) Altered expression of claudin-1, claudin-7, and tricellulin regardless of human papilloma virus infection in human tonsillar squamous cell carcinoma. Acta Otolaryngol. 2011 131:861-8

Krause, G., Winkler, L., Mueller, S. L., Haseloff, R. F., Piontek, J., and Blasig, I. E. (2008). Structure and function of claudins. Biochimica Et Biophysica Acta (BBA)—Biomembranes 1778, 631-645.

Lal-Nag, M., and Morin, P. J. (2009). The claudins. Genome Biol 10, 235-235.

Leotlela, P. D., Wade, M. S., Duray, P. H., Rhode, M. J., Brown, H. F., Rosenthal, D. T., Dissanayake, S. K., Earley, R., Indig, F. E., Nickoloff, B. J., et al. (2007). Claudin-1 overexpression in melanoma is regulated by PKC and contributes to melanoma cell motility. Oncogene 26, 3846-3856.

Liu T, Cheng W, Lai D, Huang Y, Guo L. (2010) Characterization of primary ovarian cancer cells in different culture systems. Oncol Rep. 23:1277-84.

Lu, S., Singh, K., Mangray, S., Tavares, R., Noble, L., Resnick, M. B., and Yakirevich, E. (2012). Claudin expression in high-grade invasive ductal carcinoma of the breast: correlation with the molecular subtype. Modern Pathology.

Miwa, N., Furuse, M., Tsukita, S., Niikawa, N., Nakamura, Y., and Furukawa, Y. (2001). Involvement of claudin-1 in the beta-catenin/Tcf signaling pathway and its frequent upregulation in human colorectal cancers. Oncol. Res 12, 469-476.

Myal Y, Leygue E, Blanchard A A. (2010) Claudin 1 in breast tumorigenesis: revelation of a possible novel "claudin high" subset of breast cancers. J Biomed Biotechnol 2010:956897.

Nakanishi K, Ogata S, Hiroi S, Tominaga S, Aida S, Kawai T. (2008) Expression of occludin and claudins 1, 3, 4, and 7 in urothelial carcinoma of the upper urinary tract. Am J Clin Pathol. 130:43-9.

Németh, J., Németh, Z., Tatrai, P., Peter, I., Somorácz, A., Szász, A. M., Kiss, A., and Schaff, Z. (2010). High expression of claudin-1 protein in papillary thyroid tumor and its regional lymph node metastasis. Pathol. Oncol. Res. 16, 19-27.

Olive, M., Untawale, S., Coffey, R. J., Siciliano, M. J., Wildrick, D. M., Fritsche, H., Pathak, S., Cherry, L. M., Blick, M., and Lointier, P. (1993). Characterization of the DiFi rectal carcinoma cell line derived from a familial adenomatous polyposis patient. In Vitro Cell. Dev. Biol. 29A, 239-248.

Ouban A, Hamdan H, Hakam A, Ahmed A A. (2012) Claudin-1 expression in squamous cell carcinomas of different organs: comparative study of cancerous tissues and normal controls. Int J Surg Pathol. 20:132-8.

Santoro, L., Boutaleb, S., Garambois, V., Bascoul-Mollevi, C., Boudousq, V., Kotzki, P.-O., Pèlegrin, M., Navarro-Teulon, I., Pélegrin, A., and Pouget, J.-P. (2009). Noninternalizing monoclonal antibodies are suitable candidates for 125I radioimmunotherapy of small-volume peritoneal carcinomatosis. J. Nucl. Med. 50, 2033-2041.

Shin H I, Kim B H, Chang H S, Kim C I, Jung H R, Park C H. (2011) Expression of claudin-1 and -7 in clear cell renal cell carcinoma and its clinical significance. Korean J Urol. 52:317-22.

Singh, A. B., Sharma, A., and Dhawan, P. (2010). Claudin family of proteins and cancer: an overview. J Oncol 2010, 541957.

Soini Y, Kinnula V, Kahlos K, Pääkkö P. (2006) Claudins in differential diagnosis between mesothelioma and metastatic adenocarcinoma of the pleura. J Clin Pathol. 59:250-4.

Swisshelm, K., Machl, A., Planitzer, S., Robertson, R., Kubbies, M., and Hosier, S. (1999). SEMP1, a senescence-associated cDNA isolated from human mammary epithelial cells, is a member of an epithelial membrane protein superfamily. Gene 226, 285-295.

Szabó, I., Kiss, A., Schaff, Z., and Sobel, G. (2009). Claudins as diagnostic and prognostic markers in gynecological cancer. Histol. Histopathol 24, 1607-1615.

Szász, A. M., Nyirady, P., Majoros, A., Szendrõi, A., Szũcs, M., Székely, E., Tökés, A.-M., Romics, I., and Kulka, J. (2009). beta-catenin expression and claudin expression pattern as prognostic factors of prostatic cancer progression. BJU Int.

Takala H, Saarnio J, Wiik H, Soini Y. (2007) Claudins 1, 3, 4, 5 and 7 in esophageal cancer: loss of claudin 3 and 4 expression is associated with metastatic behavior. APMIS. 115:838-47.

Tsukahara M, Nagai H, Kamiakito T, Kawata H, Takayashiki N, Saito K, Tanaka A. (2005) Distinct expression patterns of claudin-1 and claudin-4 in intraductal papillary-mucinous tumors of the pancreas. Pathol Int. 55:63-9.

Tsukita, S., and Furuse, M. (2006). The Structure and Function of Claudins, Cell Adhesion Molecules at Tight Junctions Annals of the New York Academy of Sciences 915, 129-135.

Tsukita, S., Furuse, M., and Itoh, M. (2001). Multifunctional strands in tight junctions. Nat. Rev. Mol. Cell Biol. 2, 285-293.

Weber C R, Nalle S C, Tretiakova M, Rubin D T, Turner J R. (2008) Claudin-1 and claudin-2 expression is elevated in inflammatory bowel disease and may contribute to early neoplastic transformation. Lab Invest. 88:1110-20.

Wu, Y.-L., Zhang, S., Wang, G.-R., and Chen, Y.-P. (2008). Expression transformation of claudin-1 in the process of gastric adenocarcinoma invasion. World J. Gastroenterol. 14, 4943-4948.

Yoon, C.-H., Kim, M.-J., Park, M.-J., Park, I.-C., Hwang, S.-G., An, S., Choi, Y.-H., Yoon, G., and Lee, S.-J. (2009). Claudin-1 acts through c-abl-pkcdelta signaling and has a causal role in the acquisition of invasive capacity in human liver cells. J. Biol. Chem.

The invention claimed is:

1. A method of treating a colorectal cancer in a subject in need thereof comprising administering to the subject a therapeutically effective amount of an anti-claudin 1 (CLDN1) antibody that comprises either (a) a heavy chain variable region as set forth in SEQ ID NO: 1 and a light chain variable region as set forth in SEQ ID NO: 5 or (b) a heavy chain variable region comprising the three complementarity determining regions (CDRs) of the heavy chain variable region set forth in SEQ ID NO: 1 and a light chain variable region comprising the three CDRs of the light chain variable region set forth in SEQ ID NO: 5.

2. The method of claim 1 wherein the antibody is selected from the group consisting of monoclonal antibodies, Fab antibodies, F(ab')2 antibodies, TandAb dimer antibodies, Fv antibodies, scFv antibodies, dsFv antibodies, ds-scFv antibodies, Fd antibodies, minibodies, diabodies, bispecific antibody fragments, bibodies, tribodies, sc-diabodies, kappa (lamda) bodies (scFv-CL fusions); BiTE antibodies; DVD-Ig antibodies; SIP antibodies; SMIP antibodies; and DART antibodies.

3. The method of claim 1 wherein the antibody is a humanized antibody or a chimeric antibody.

4. The method of claim 1 wherein the anti-CLDN1 antibody comprises a heavy chain variable region comprising SEQ ID NO:2 in the H-CDR1 region, SEQ ID NO:3 in the H-CDR2 region and SEQ ID NO:4 in the H-CDR3 region; and a light chain variable region comprising SEQ ID NO:6 in the L-CDR1 region, SEQ ID NO:7 in the L-CDR2 region and SEQ ID NO:8 in the L-CDR3 region.

5. The method of claim 1 wherein the anti-CLDN1 antibody is an antibody drug conjugate.

6. The method of claim 5 wherein the anti-CLDN1 antibody is conjugated to a cytotoxic agent.

7. The method of claim 5 wherein the anti-CLDN1 antibody is conjugated to therapeutic agent selected from the group consisting of chemotherapeutic agents, prodrug converting enzymes, radioactive isotopes or compounds, and toxins.

8. The method of claim 6 wherein the cytotoxic agent is selected from the group consisting of antitubulin agents, auristatins, DNA minor groove binders, DNA replication inhibitors, alkylating agents, anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, and vinca alkaloids.

9. The method of claim 6 wherein the cytotoxic agent is selected from the group consisting of androgen, anthramycin (AMC), asparaginase, 5-azacytidine, azathioprine, bleomycin, busulfan, buthionine sulfoximine, camptothecin, carboplatin, carmustine, CC-1065, chlorambucil, cisplatin, colchicine, cyclophosphamide, cytarabine, cytidine arabinoside, cytochalasin B, dacarbazine, dactinomycin, daunorubicin, decarbazine, docetaxel, doxorubicin, an estrogen, 5-fluordeoxyuridine, etopside phosphate, 5-fluorouracil, gramicidin D, hydroxyurea, idarubicin, ifosfamide, irinotecan, lomustine, mechlorethamine, melphalan, 6-mercaptopurine, methotrexate, mithramycin, mitomycin C, mitoxantrone, nitroimidazole, paclitaxel, plicamycin, procarbizine, streptozotocin, tenoposid, 6-thioguanine, thioTEPA, topotecan, vinblastine, vincristine, and vinorelbine.

10. The method of claim 6 wherein the cytotoxic agent is selected from the group consisting of doxorubicin, paclitaxel, melphalan, vinca alkaloids, methotrexate, mitomycin C and etoposide.

11. The method of claim 6 wherein the cytotoxic agent is auristatin E or a derivative thereof.

12. The method of claim 5 wherein the anti-CLDN1 antibody is conjugated to a pro-drug converting enzyme.

13. The method of claim 12 wherein the pro-drug converting enzyme is selected from the group consisting of carboxypeptidase G2, beta-glucuronidase, penicillin-V-amidase, penicillin-G-amidase, beta-lactamase, beta-glucosidase, nitroreductase and carboxypeptidase A.

14. The method of claim 1 wherein the anti-CLDN1 antibody is used to induce antibody dependent cellular cytotoxicity (ADCC) or complement dependent cytotoxicity (CDC).

15. The method of claim 1 wherein the anti-CLDN1 antibody is a bispecific antibody comprising one binding site for CLDN1 and a second binding side for an activating trigger molecule on an effector cell.

16. The method of claim 15 wherein the trigger molecule on an effector cell is selected from the group consisting of CD3 on T-cells, CD16 on natural killer cells, monocytes and macrophages, CD89 and CD64 on neutrophils and monocytes/macrophages, and DEC-205 on dendritic cells.

* * * * *

SEQUENCE LISTING

<160> NUMBER OF SEQ ID NOS: 8

<210> SEQ ID NO 1
<211> LENGTH: 120
<212> TYPE: PRT
<213> ORGANISM: Artificial
<220> FEATURE:
<223> OTHER INFORMATION: Synthetic VH

<400> SEQUENCE: 1

Gln Ile Gln Leu Val Gln Ser Gly Pro Glu Leu Lys Lys Pro Gly Glu
1               5                   10                  15

Thr Val Arg Ile Ser Cys Lys Ala Ser Gly Tyr Thr Phe Thr Thr Ser
            20                  25                  30

Gly Met Gln Trp Leu Gln Lys Met Pro Gly Lys Gly Leu Lys Trp Ile
        35                  40                  45

Gly Trp Ile Asn Thr His Phe Gly Glu Pro Lys Tyr Ala Glu Asp Phe
    50                  55                  60

Lys Gly Arg Phe Ala Phe Ser Leu Glu Thr Ser Ala Ser Thr Ala Tyr
65                  70                  75                  80

Leu Gln Ile Ser Asn Leu Lys Asn Glu Asp Thr Ala Thr Tyr Phe Cys
                85                  90                  95

Ala Gly Ala Gly Tyr Tyr Gly Ser Arg Tyr Phe Asp Val Trp Gly Ala
            100                 105                 110

Gly Thr Thr Val Thr Val Ser Ser
        115                 120

<210> SEQ ID NO 2
<211> LENGTH: 8
<212> TYPE: PRT
<213> ORGANISM: Artificial
<220> FEATURE:
<223> OTHER INFORMATION: Synthetic VH-CDR1

<400> SEQUENCE: 2

Gly Tyr Thr Phe Thr Thr Ser Gly
1               5

<210> SEQ ID NO 3
<211> LENGTH: 8
<212> TYPE: PRT
<213> ORGANISM: Artificial
<220> FEATURE:
<223> OTHER INFORMATION: Synthetic VH-CDR2

<400> SEQUENCE: 3

Ile Asn Thr His Phe Gly Glu Pro
1               5

<210> SEQ ID NO 4
<211> LENGTH: 13
<212> TYPE: PRT
<213> ORGANISM: Artificial
<220> FEATURE:
<223> OTHER INFORMATION: Synthetic VH-CDR3

<400> SEQUENCE: 4

Ala Gly Ala Gly Tyr Tyr Gly Ser Arg Tyr Phe Asp Val
1               5                   10

<210> SEQ ID NO 5
<211> LENGTH: 107
<212> TYPE: PRT

```
<213> ORGANISM: Artificial
<220> FEATURE:
<223> OTHER INFORMATION: Synthetic VL

<400> SEQUENCE: 5

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Ser Tyr Pro Leu
                85                  90                  95

Thr Phe Gly Gly Gly Thr Lys Leu Glu Ile Lys
            100                 105

<210> SEQ ID NO 6
<211> LENGTH: 6
<212> TYPE: PRT
<213> ORGANISM: Artificial
<220> FEATURE:
<223> OTHER INFORMATION: Synthetic VL-CDR1

<400> SEQUENCE: 6

Gln Asn Val Gly Thr Ala
1               5

<210> SEQ ID NO 7
<211> LENGTH: 3
<212> TYPE: PRT
<213> ORGANISM: Artificial
<220> FEATURE:
<223> OTHER INFORMATION: Synthetic VL-CDR2

<400> SEQUENCE: 7

Ser Ala Ser
1

<210> SEQ ID NO 8
<211> LENGTH: 9
<212> TYPE: PRT
<213> ORGANISM: Artificial
<220> FEATURE:
<223> OTHER INFORMATION: Synthetic VL-CDR3

<400> SEQUENCE: 8

Gln Gln Tyr Ser Ser Tyr Pro Leu Thr
1               5
```